(12) United States Patent
Goddard et al.

(10) Patent No.: US 9,883,933 B2
(45) Date of Patent: Feb. 6, 2018

(54) MEDICAL DEVICE AND METHOD OF DELIVERING THE MEDICAL DEVICE

(71) Applicant: Boston Scientific Scimed, Inc., Maple Grove, MN (US)

(72) Inventors: James Goddard, Pepperell, MA (US); Peter J. Pereira, Mendon, MA (US); Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 362 days.

(21) Appl. No.: 14/463,144

(22) Filed: Aug. 19, 2014

(65) Prior Publication Data

US 2015/0057491 A1    Feb. 26, 2015

Related U.S. Application Data

(60) Provisional application No. 61/870,027, filed on Aug. 26, 2013.

(51) Int. Cl.
    *A61F 2/04*         (2013.01)
    *A61F 2/00*         (2006.01)

(52) U.S. Cl.
    CPC .......... *A61F 2/0022* (2013.01); *A61F 2/0045* (2013.01); *A61F 2/0063* (2013.01);
    (Continued)

(58) Field of Classification Search
    CPC ...... A61F 2250/0014; A61F 2250/0029; A61F 2230/006; A61F 2230/0069;
    (Continued)

(56) References Cited

U.S. PATENT DOCUMENTS 5,147,374 A * 9/1992 Fernandez ............ A61F 2/0063
                                         606/151
6,575,897 B1 6/2003 Ory et al.
(Continued)

FOREIGN PATENT DOCUMENTS

FR          2859624 A1    3/2005
FR          2912761 A1    8/2008
(Continued)

OTHER PUBLICATIONS

Non-Final Office Action for U.S. Appl. No. 14/204,985, dated Feb. 12, 2016, 12 pages.
(Continued)

*Primary Examiner* — Charles A Marmor, II
*Assistant Examiner* — Thaddeus Cox
(74) *Attorney, Agent, or Firm* — Brake Hughes Bellermann LLP

(57) ABSTRACT

The invention discloses an implant. The implant may include a first flap and a second flap. The first flap may further include a first portion, a second portion and a transition region. The first portion may be configured to be attached proximate a sacrum. The second portion may be configured to be attached to an anterior vaginal wall. The transition region lies between the first portion and the second portion. The second flap may be fabricated such that a portion of the second flap is configured to be attached to a posterior vaginal wall. The implant may be configured such that a value corresponding to a biomechanical parameter defining a biomechanical attribute of the portion of the first flap attaching to the anterior wall is different from a value of the biomechanical parameter defining the biomechanical attribute of the portion of the second flap attaching to the posterior wall.

14 Claims, 13 Drawing Sheets

(52) U.S. Cl.
CPC . *A61F 2220/0008* (2013.01); *A61F 2230/006* (2013.01); *A61F 2250/0029* (2013.01); *A61F 2250/0037* (2013.01)

(58) Field of Classification Search
CPC ............ A61F 2230/0067; A61F 2/0004; A61F 2/0031; A61F 2/0036; A61F 2/0045; A61F 2/0063
See application file for complete search history.

(56) References Cited

U.S. PATENT DOCUMENTS

| | | | |
|---|---|---|---|
| 2004/0138747 A1 | 7/2004 | Kaladelfos et al. | |
| 2005/0234291 A1 | 10/2005 | Gingras | |
| 2005/0243291 A1 | 11/2005 | Kim et al. | |
| 2006/0130848 A1 | 6/2006 | Carey | |
| 2007/0142698 A1* | 6/2007 | Bourne | A61F 2/0045 600/30 |
| 2008/0177132 A1 | 7/2008 | Alinsod et al. | |
| 2008/0208360 A1 | 8/2008 | Meneghin et al. | |
| 2009/0156891 A1 | 6/2009 | Heys et al. | |
| 2009/0171377 A1 | 7/2009 | Intoccia et al. | |
| 2009/0326565 A1 | 12/2009 | Trabucco et al. | |
| 2010/0305394 A1* | 12/2010 | Rosenblatt | A61F 2/0063 600/30 |
| 2011/0021869 A1 | 1/2011 | Cholhan | |
| 2011/0224703 A1 | 9/2011 | Mortarino et al. | |
| 2012/0108894 A1* | 5/2012 | Young | A61F 2/0045 600/37 |
| 2013/0109910 A1* | 5/2013 | Alexander | A61B 17/00234 600/37 |
| 2013/0281768 A1* | 10/2013 | Dolan | A61F 2/0045 600/37 |
| 2014/0257030 A1 | 9/2014 | Li et al. | |
| 2014/0275753 A1 | 9/2014 | Nagale et al. | |
| 2014/0275754 A1 | 9/2014 | Pereira et al. | |
| 2014/0275755 A1 | 9/2014 | Pereira et al. | |
| 2015/0032144 A1* | 1/2015 | Holloway | A61F 2/013 606/200 |

FOREIGN PATENT DOCUMENTS

| | | |
|---|---|---|
| WO | 2000074594 A1 | 12/2000 |
| WO | 2008048971 A2 | 4/2008 |
| WO | 2010087923 A1 | 8/2010 |
| WO | 2014165211 A2 | 10/2014 |
| WO | 2014165211 A3 | 12/2014 |
| WO | 2015031131 A1 | 3/2015 |

OTHER PUBLICATIONS

Non Final Office Action for U.S. Appl. No. 14/206,971, dated Mar. 9, 2016, 15 Pages.
Non Final Office Action for U.S. Appl. No. 14/206,971, dated Aug. 28, 2015, 19 Pages.
First Examination Report for AU Application No. 2014248547, dated Apr. 11, 2016, 3 Pages.
International Preliminary Report on Patentability for PCT Application No. PCT/US14/24804, dated Sep. 24, 2015, 9 Pages.
International Search Report and Written Opinion for PCT Application No. PCT/US2014/024804, dated Oct. 16, 2014, 13 Pages.
Invitation to Pay Add'l Fees and Partial Search Report for PCT Application No. PCT/US2014/024804, dated Jul. 22, 2014, 5 Pages.
International Preliminary Report on Patentability for PCT Application No. PCT/US2014/051897, dated Mar. 10, 2016, 8 pages.
International Search Report and Written Opinion for PCT Application No. PCT/US2014/051897, dated Nov. 4, 2014, 13 pages.
Office Action for European Application 14761926.6, dated Dec. 9, 2016, 3 pages.

\* cited by examiner

MEDICAL DEVICE AND METHOD OF DELIVERING THE MEDICAL DEVICE

BACKGROUND

Field

This application is a Nonprovisional of, and claims priority to, U.S. Patent Application No. 61/870,027, filed Aug. 26, 2013, entitled "MEDICAL DEVICE AND METHOD OF DELIVERING THE MEDICAL DEVICE", which is incorporated by reference herein in its entirety.

The present invention generally relates to medical devices and procedures, and particularly, devices configured to be delivered and placed in a patient's body for the treatment of pelvic floor disorder and methods thereof.

Description of the Related Art

Pelvic organ prolapse is an abnormal descent or herniation of the pelvic organs. A prolapse may occur when muscles and tissues in the pelvic region become weak and can no longer hold the pelvic organs in place correctly.

Treatment for symptoms of the pelvic organ prolapse can include changes in diet, weight control, and lifestyle. Treatment may also include surgery, medication, and use of grafts to support the pelvic organs.

Sacrocolpopexy is one such surgical technique that may be used to repair pelvic organ prolapse. This can be performed using an open abdominal technique or with the use of minimally invasive surgery, such as laparoscopy or robotic-assisted surgery. The technique includes suspension of the apical portion of vagina (or sometimes the vaginal cuff after hysterectomy) using an implant such that the technique tries to recreate the natural anatomic support.

In some cases, a Y-shaped implant may be used to treat vaginal vault prolapse during the sacrocolpopexy procedure. The Y-shaped implant aids vaginal cuff suspension to the sacrum and provides long-term support. The procedure can be minimally invasive (laparoscopic sacral colpopexy) or traditional (open sacral colpopexy). Also, in some cases, different anatomical locations inside a patient's body for example, vagina, uterus, and sacrum may be involved in repair of the pelvic organ prolapse. For example, at least a portion of the implant may be attached to an anterior vaginal wall, and a posterior vaginal wall in some cases. These anatomical locations have different biological attributes and behave differently. Therefore, the implant may not conform to the varying behavior of the different anatomical locations where the implant portions are attached.

Thus, in light of the above, there is a need for an improved implant that can be fabricated to conform to varying behavior of different anatomical locations inside a patient's body.

SUMMARY

In an embodiment, the invention discloses an implant. The implant may include a first flap and a second flap. The first flap may further include a first portion, a second portion and a transition region. The first portion may be configured to be attached proximate a sacrum. The second portion may be configured to be attached to an anterior vaginal wall. The transition region lies between the first portion and the second portion. The second flap may be fabricated such that a portion of the second flap is configured to be attached to a posterior vaginal wall. The implant may be configured such that a value corresponding to a biomechanical parameter defining a biomechanical attribute of the portion of the first flap attaching to the anterior wall is different from a value of the biomechanical parameter defining the biomechanical attribute of the portion of the second flap attaching to the posterior wall.

In an embodiment, the invention discloses a tubular implant. The tubular implant includes a first portion, a second portion, and a transition region. The first portion of the tubular implant can be configured to be attached proximate a sacrum. The transition region can extend from the first portion. The second portion can extend from the transition region monolithically. The second portion includes a first section and a second section and two slits provided laterally in the second portion configuring the first section as apart from the second section at a proximal end. The tubular implant further includes a lumen defined within the first and second portions of the tubular implant. The tubular implant can be configured such that the first section is configured to be attached to an anterior vaginal wall, and the second section is configured to be attached to a posterior vaginal wall.

In an embodiment, the invention discloses a method for placing an implant in a body of a patient. The method includes inserting the implant inside the body. The method further includes attaching a portion of the implant to an anterior vaginal wall, wherein the portion attaching to the anterior vaginal wall defines a first value of a biomechanical parameter defining a biomechanical attribute. The method further includes attaching a portion of the implant to a posterior vaginal wall. The portion attaching to the posterior vaginal wall defines a second value of the biomechanical parameter such that the second value corresponding to the portion attaching to the posterior wall is different from the first value corresponding to the portion attaching to the anterior wall.

BRIEF DESCRIPTION OF THE FIGURES

The invention and the following detailed description of certain embodiments, thereof, may be understood with reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating vaginal prolapse. However, the invention may be equally employed for other treatment purposes such as pelvic organ prolapse or other pelvic disorders such as incontinence. As described below in various illustrative embodiments, the invention provides systems, methods, and devices employing a medical device configured to deliver or place an implant within a patient's body to support pelvic organs and deliver a fluid such as a medication inside the body such as to the implant site for the treatment of pelvic organ prolapse or other pelvic disorders.

The term patient may be used hereafter for a person who benefits from the medical device or the methods disclosed in the present invention. For example, the patient may be a person whose body is operated with the use of the medical device disclosed by the present invention in a surgical treatment. For example, in some embodiments, the patient may be a human female, human male or any other mammal.

The terms proximal and distal described in relation to various devices, apparatuses, and components as discussed in the subsequent text of the present invention are referred to with a point of reference. The point of reference, as used in this description, is a perspective of an operator. The operator may be a surgeon, a physician, a nurse, a doctor, a technician, and the like who may perform the procedure of delivery and placement of the bodily implants into the patient's body as described in the present invention. The term proximal refers to an area that is closest to the operator. The term distal refers to an area that is farthest from the operator.

Figure 1:
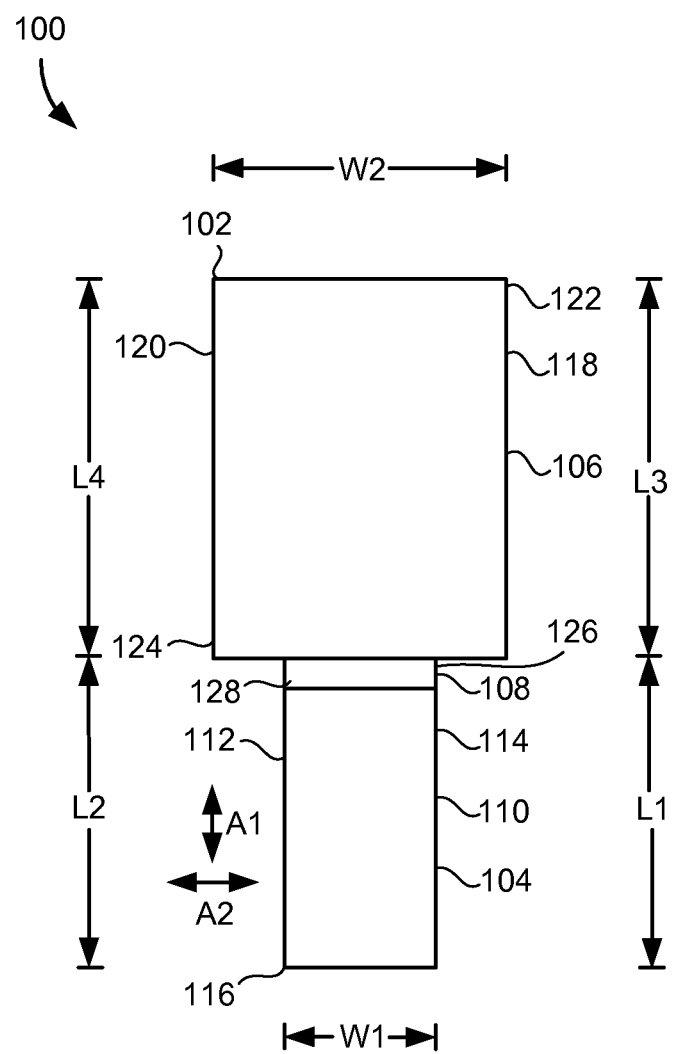
FIG. 1 is a schematic diagram of a medical assembly for treatment of a pelvic floor disorder, in accordance with an embodiment of the invention.

FIG. 1 is a schematic diagram of an implant 100. The implant 100 can include a first flap 102. The first flap 102 can include a first portion 104, a second portion 106 and a transition region 108. In an embodiment, the implant 100 can be used for the treatment of a pelvic floor disorder. In some embodiments, the implant 100 can be used to suspend various bodily locations in a body of a patient. For example, in some embodiments, the implant 100 can be used to suspend a pelvic organ of a patient's body. In some embodiments, the implant 100 can be a part of a retropubic incontinence sling. In some embodiments, the implant 100 can be configured to be delivered by way of a transvaginal approach or a transobturator approach or vaginal pre-pubic approach or a laparoscopic approach or can be delivered through other approaches and positioned at various locations within a patient's body.

The first portion 104 defines a first side 110, a second side 112, a proximal portion 114 and a distal portion 116. The proximal portion 114 can be attached to or extend from the transition region 108 of the first flap 102. The distal portion 116 can be configured to be attached to a first bodily tissue. In some embodiments, the first bodily tissue can be a sacrum or tissue proximate a sacrum of a patient. In some embodiments, the first bodily tissue can be any one of lumbar vertebra, tail bone, and illium portion of hip bone inside the patient's body. In some embodiments, the first bodily tissue can be any other location inside the patient's body.

The first portion 104 defines a length L1 along the first side 110 extending from the proximal portion 114 to the distal portion 116. The first portion 104 defines a length L2 along the second side 112 extending from the proximal portion 114 to the distal portion 116. In some embodiments, the length L1 can be equal to the length L2. In some embodiments, the length L1 can be different from the length L2. The first portion 104 defines a width W1 extending between the first side 110 and the second side 112. In some embodiments, the width W1 can remain constant from the proximal portion 114 to the distal portion 116. In some embodiments, the width W1 can differ from the proximal portion 114 to the distal portion 116.

The first bodily tissue exhibits a definite biomechanical behavior in a defined set of physical conditions. The first portion 104 can be configured to define a set of biomechanical attributes or biomechanical properties so as to emulate the biomechanical behavior of the first bodily tissue, where at least a portion of the first portion 104 is required to be attached, in the defined set of physical conditions. The biomechanical attributes for the first bodily tissue can be defined by a first set of values of respective biomechanical parameters associated with each of the biomechanical attributes. For example, in some embodiments, the biomechanical attribute can be elasticity and a corresponding biomechanical parameter can be modulus of elasticity which can be defined by a numerical value. While the use of a modulus (such as a modulus of elasticity) is used to measure a biomechanical parameter, it should be understood that the biomechanical parameter of the bodily tissue may also be directly measured. For example, in some embodiments, the elasticity of the bodily tissue maybe measured (without using a modulus). In some embodiments, the biomechanical attribute can be stiffness. In some embodiments, the biomechanical attribute can be strength. In some embodiments, the biomechanical attribute can be resistance to creep. In various embodiments, the biomechanical attributes of the first portion 104 can be defined for example by defining one or more of shape, size, fabrication method, structure, profile, knit structure, pore size, material of fabrication, fiber orientation, and the like. In some embodiments, for example, the congruence between the biomechanical behavior of the first bodily tissue and the first portion 104 can be achieved by varying the shape of the first portion 104. For example, the first portion 104 can have a square, rectangular, triangular or any other shape, which can facilitate the first portion 104 in closely equating the biomechanical behavior of the first bodily tissue.

In some embodiments, the biomechanical attributes of the first portion 104 can be defined by a first type of knit structure (not shown here and explained later). In some embodiments, the first type of knit structure can be defined by first type of knitting pattern (not shown here and explained later). In some embodiments, the first type of knit structure can be defined by a first type of pore construct. In some embodiments, the first type of knit structure can be defined by weaving the knit with a required and defined tension. For example, the first knitting pattern can be woven tightly or loosely to define required type of knitting pattern. In some embodiments, the first knitting pattern characterized by biomechanical properties of high elastic modulus and stiffness can facilitate holding onto bodily tissue such as the vagina, the vaginal apex, or a sacrum in the correct anatomical location. The different ways of achieving the desirable biomechanical attributes for the first portion 104 of the first flap 102 can be used in isolation or in combination. It must be appreciated that though the above ways of defining the required biomechanical attributes are used for mesh-based implants 100 including a knit pattern, the implant 100 can be fabricated as a planar structure. In such embodiments, the biomechanical attributes of the first portion 104 of the first flap 102 of the implant 100 can be defined for example by the material used in fabrication of the first portion 104, shape and size of the portion, and the like without limitations. For example, a rigid medical grade polymer can be used for fabricating the first portion 104 thereby defining the biomechanical attribute of rigidity for the first portion 104 to a desired value.

In some embodiments, reinforcements such as reinforcement fibers may be woven into portions of the implant 100. In some embodiments, the implant 100 may include elastic fibers woven into portions of the implant 100.

The second portion 106 defines a first side 118, and a second side 120, a proximal portion 122 and a distal portion 124. The distal portion 124 can be attached to or extend from the transition region 108 of the first flap 102. The proximal portion 122 can be configured to be attached to a second bodily tissue. In some embodiments, the second bodily tissue can be an anterior vaginal wall inside a patient's body. In some embodiments, the second bodily tissue can be at least one of a posterior vaginal wall, a uterus, and a vaginal apex. In some embodiments, the second bodily tissue can be any other location inside the patient's body.

The second portion 106 defines a length L3 along the first side 118 extending from the proximal portion 122 to the distal portion 124. The second portion 106 defines a length L4 along the second side 120 extending from the proximal portion 122 to the distal portion 124. In some embodiments, the length L3 can be equal to the length L4. In some embodiments, the length L3 can be different from the length L4. The second portion 106 defines a width W2 extending between the first side 118 and the second side 120. In some embodiments, the width W2 can remain constant from the proximal portion 122 to the distal portion 124. In some embodiments, the width W2 can differ from the proximal portion 122 to the distal portion 124. In some embodiments, the second portion 106 is fabricated such that the width W2 of the second portion 106 is greater than the width W1 of the first portion 104. In some embodiments, the second portion 106 can define a trapezoidal shape such that the width W2 at the proximal portion 122 is substantially greater than the width W2 at the distal portion 124. In some embodiments, the second portion 106 can have a polygonal shape. In some embodiments, the second portion 106 can have a square, rectangular, triangular or any other shape.

The second bodily tissue exhibits a definite biomechanical behavior in a defined set of physical conditions. The behavior exhibited by the second bodily tissue can be different than the behavior exhibited by the first bodily tissue. The second portion 106 can be configured to define the biomechanical attributes or biomechanical properties so as to emulate the biomechanical behavior of the second bodily tissue in the defined set of physical conditions. The biomechanical attributes can be defined by a second set of values of respective biomechanical parameters associated with each of the biomechanical attributes. Consequently, the second portion 106 may be defined to exhibit values of the biomechanical attributes, different than the values of the biomechanical attributes of the first portion 104, in accordance with the second bodily tissue where at least a portion of the second portion 106 of the first flap 102 may be attached. It must be appreciated that in some embodiments, only one or more but not all of the first set of values biomechanical attributes and the second set of values differ in terms of their values of parameters defining the respective attributes. For example, the modulus of elasticity may be same for the first portion 104 and the second portion 106 but any other parameter for other attribute such as resistance to creep may be different. In some other embodiments, all the attributes of the first portion 104 and the second portion 106 may differ in terms of their numerical values of parameters defining the respective attributes.

In some embodiments, the second set of values associated with the biomechanical attributes can be different along different directions for the same fixed set of physical conditions even for the same attribute. For example, in some embodiments, a value of a parameter P defining an attribute T along a first direction A1 can be different from a value of the parameter P defining the attribute T along a second direction A2. In some embodiments, the first direction A1 can be a longitudinal direction and the second direction A2 can be a transverse or perpendicular direction. In other embodiments, the first direction can be disposed at a non-transverse or non-perpendicular angle with respect to the second direction.

In some embodiments, the thread diameter, and/or the thread count may contribute to the different the biomechanical attributes. In some embodiments, the thickness of the mesh may contribute to the different biomechanical attributes. In some embodiments, the sides or edges of the mesh may have rough surfaces or projecting fibers.

It must be appreciated that the biomechanical behavior of the bodily tissues and the biomechanical attributes of the various portions of the implant 100 may change owing to change in physical conditions. Therefore, for the purpose of comparing the various biomechanical behaviors and the biomechanical attributes, a reasonably sufficient amount of similarity in physical conditions may be assumed to an extent that a change in the conditions creates an ignorable influence. However, in other embodiments, the physical conditions may vary and measurement of the biomechanical behavior and the attributes may accordingly be calibrated so as to compare the various values associated with the various attributes in light of the required characteristics at the required locations. For example, the stiffness of the first portion 104 and the second portion 106 may be different initially during fabrication but since the physical conditions at the respective bodily tissues may be different, therefore the initial values of the stiffness may not remain same after placement. This change due to variation in the physical conditions may be considered while defining the attributes of the respective portions of the implant 100 so as to achieve the desired set of attributes with the desired set of values.

In some embodiments, the biomechanical attributes can include elasticity and a corresponding biomechanical parameter can be modulus of elasticity. In some embodiments, the biomechanical attribute can be viscoelasticity. In some embodiments, the biomechanical attribute can be viscohyperelasticity. In some embodiments, the biomechanical attribute can be anisotropic. In various embodiments, the biomechanical attributes of the second portion 106 can be defined by defining one or more of shape, size, fabrication method or structure, profile, knit structure, pore size, material of fabrication, and the like. In some embodiments, for example, the congruence between the biomechanical behavior of the second bodily tissue and the second portion 106 can be achieved by varying the shape of the second portion 106. For example, the trapezoidal shape of the second portion 106 can conform to shape of the second bodily tissue such as the anterior vaginal wall inside a patient's body.

In some embodiments, the biomechanical attributes of the second portion 106 can be defined a second type of knit structure (not shown here and explained later). In some embodiments, the second type of knit structure can be defined by second type of knitting pattern (not shown here and explained later). In some embodiments, the second type of knit structure can be defined by weaving the knit with a required and defined tension. For example, the anterior vaginal wall shows anisotropic biomechanical behavior, with a bias toward more elongation along a transverse direction (or non-transverse direction), therefore, the second type of knitting pattern can be selected so as to be more elastic along a longitudinal direction as compared to the transverse direction.

In some embodiments, the second type of knit structure can be defined by a second type of pore construct. In some embodiments, the second type of pore construct is different from the first type of pore construct. In some embodiments, the second pore construct includes a larger pore size as compared to a pore size of the first pore construct. In some embodiments, the difference in pore constructs of the first and second portions 104 and 106 can be achieved by knitting or weaving a mesh with different pore sizes. In some embodiments, the difference in pore constructs for the first and second portions 104 and 106 can be achieved by extruding a single pore size mesh and heat setting the pores to set a different pore size for the first and second portions 104 and 106 as illustrated and described by later figures. The second pore construct can define the second set of values of the biomechanical attributes of the second portion 106. In an embodiment, the second pore construct can define larger pore sizes as compared to the remaining portion of the implant 100. In some embodiments, the second pore construct can be fabricated to exhibit biomechanical attributes of high flexibility and elongation to a particular strain level and high stiffness after the particular stain level is reached. Such a strain behavior may closely emulate the biomechanical behavior of the vaginal wall for example the anterior vaginal wall. Therefore, the second pore structure defines the biomechanical attributes so as to conform to the biomechanical behavior of the second bodily tissue that is the vaginal wall.

In some embodiments, the apertures formed by the mesh material may be of any shape or size. In some embodiments, the mesh material may be formed in more than one portion or strip rather than a single portion. In some embodiments, the mesh material may include a coating or covering. In some embodiments, the fibers of the mesh may be disposed at any angle with respect to other fibers of the mesh. In some embodiments, the fibers are woven perpendicular to other fibers of the mesh. In other embodiments, the fibers are woven at different angles. In some embodiments, the mesh may be compress or annealed.

In some embodiments, the values associated with the biomechanical attributes can be defined by a material used for fabricating the second portion 106. For example, a viscoelastic medical grade polymer can be used for fabricating the second portion 106 thereby defining a value for the biomechanical attribute of viscoelasticity for the second portion 106. In some embodiments, an anisotropic medical grade polymer can be used for achieving a desired anisotropic value. In some embodiments, a creep resistant medical grade polymer can be used for achieving a desired value of creep resistance.

In some embodiments, the first bodily tissue can be stiffer and the second bodily tissue can be flexible, therefore the first portion 104 in such cases can be configured with the biomechanical attributes congruent with high stiffness and the second portion 106 with high flexibility. Similarly, in other embodiments, other attributes may be associated according to the behavior of the respective bodily tissues. The different ways of achieving the desirable values for the biomechanical attributes for the first portion 104 and the second portion 106 as discussed above can be used in isolation or in combination.

In some embodiments, for example, the second bodily tissue can be the anterior vaginal wall. Various examples of attributes possibly needed to be considered for defining the portions of the first flap 102 that are attached to the anterior vaginal wall can without limitations be viscoelasticity, viscohyper-elasticity, resistance to creep and anisotropy, and the like.

The first flap 102 further includes the transition region 108 as mentioned above. The transition region 108 defines a proximal portion 126 and a distal portion 128. The proximal portion 126 of the transition region 108 can be coupled to or extend from the distal portion 124 of the second portion 106. The distal portion 128 of the transition region 108 can be coupled to or extend from the proximal portion 114 of the first portion 104. In some embodiments, the transition region 108 may define a third type of knit structure (not shown here and explained later) that monolithically joins the first portion 104 and the second portion 106. In some embodiments, the third knit structure may define a third type of pore construct (not shown here and explained later). In some embodiments, the first flap 102 can be formed by suturing together the first portion 104 and the second portion 106. In such cases, the transition region 108 includes sutures tying the first portion 104 and the second portion 106.

In some embodiments, the implant 100 further includes a second flap (not shown in FIG. 1). The second flap can include a first portion, a second portion and a transition region. The first portion and the transition region of the second flap can function the same way as that of the first flap 102 and can be defined in a similar manner. The first portion can be attached to the first bodily tissue proximate to a location where the first portion 104 of the first flap 102 is attached. The second portion of the second flap can be configured to be attached to a third bodily tissue. In some embodiments, the third bodily tissue can be a posterior vaginal wall inside a patient's body. The third bodily tissue exhibits a definite biomechanical behavior in a defined set of physical conditions. The second portion can define the biomechanical attributes so as to emulate the biomechanical behavior of the third bodily tissue, where at least a portion of the first portion of the second flap is required to be attached, in the defined set of physical conditions. The biomechanical attributes can be defined by a third set of values corresponding to respective biomechanical parameters associated with the biomechanical attributes. The second portion of the second flap can be configured so that at least one of the biomechanical parameters of the second portion 106 of the first flap and the second portion of the second flap differ in their numerical values. For example, the stiffness behavior of the anterior vaginal wall can be different from the posterior vaginal wall; therefore the second portion 106 of the first flap 102 and the second portion of the second flap can be fabricated to exhibit stiffness attributes different from each other.

In some embodiments, the implant 100 can be configured such that each of the first flap 102 and the second flap define strips of material and can be configured to be attached separately to bodily locations. In some embodiments, each of the first flap 102 and the second flap are constructed from a single piece of material. In some embodiments, the first flap 102 and the second flap are fabricated independent of each other. In some embodiments, the implant 100 can be formed from a mesh material. In some embodiments, the implant can be formed from a non-mesh material.

In some embodiments, the implant 100 can be Y-shaped. The Y-shaped implant can include three portions—a first portion configured to be attached to the sacrum or tissues proximate to the sacrum, a second portion configured to be attached to the anterior vaginal wall, a third portion configured to be attached to the posterior vaginal wall. In some embodiments, the Y-shaped implant 100 can be fabricated so as to include either of the first flap 102 and the second flap as described above and another flap which may be either a conventional strip of implant material or any of the first flap and the second flap above. For example, in an embodiment, the Y-shaped implant can be fabricated by using the first flap and the second flap and coupling them together to provide a Y-shape to the implant. During fabrication a portion of the first and/or second flaps may be removed to configure the implant in the Y-shape. For example, at least one of the first portion of the first flap and the first portion of the second flap can be removed. In another embodiment, the Y-shaped implant can be fabricated by using one of the first flap and the second flap and another conventional flap such that the conventional flap can be coupled to the other of the first or the second flap to configure the implant in the Y-shape. In still another embodiment, the Y-shape can be achieved by using various portions of the first flap and the second flap and a conventional implant strip. In some embodiments, the biomechanical attributes of the three portions of the Y-shaped implant can be defined based on the biomechanical behavior of the three locations of the body where the three portions of the implant are configured to be attached. In other embodiments, the implant has a shape other than a Y-shape. For example, the implant could be rectangular, square, or any other shape. Additionally, in some embodiments, the implant has more than one portion, such as more than one separate portion. For example, the implant may have two, three or more separate portions or pieces.

In some embodiments, the implant 100, or the first flap 102 or the second flap can be cut from a prefabricated structure including the first portion 104 with the first type of knit structure and the second portion 106 with the second type of knit structure. In some embodiments, the implant 100 can be fabricated by coupling different strips of materials each defining a set of biomechanical attributes congruent with biomechanical behavior of respective anatomical locations where they are placed inside a patient's body. The strips can take a shape such as linear or planar, curvilinear, curved, or any other shape.

In some embodiments, the first flap 102 and the second flap can be monolithically defined as a single piece such as in the form of a tubular structure (not shown here and explained later). The tubular structure can include a first portion, a transition region and a second portion. The first portion can be configured to be attached proximate the sacrum inside a patient's body. In some embodiments, the first portion can be similar to the first portion of the first flap described above in terms of biomechanical attributes. The transition region extends from the first portion. In some embodiments, the second portion of the tubular structure can function in a manner similar to the way the second portion of the first flap and the second portion of the second flap together perform. For example, an upper circumferential section of the second portion of the tubular structure can function similar to the function of the second portion of the first flap and the lower circumferential section of the tubular structure can function similar to the second portion of the second flap. In an embodiment, the second portion of the tubular structure can be configured to be cut by an operator to convert it into two sections. The sections though may still be joined at a medial portion or proximate the transition region. In some embodiments, two slits may be provided along two lateral edges of the tubular structure to define the two flaps for the two different bodily tissues. The slits can be made by an operator or may be predefined.

In some embodiments, the procedure of placing the implant 100 within a body can be performed after performing hysterectomy and removal of uterus from the body. In some other embodiments, the implant 100 can be placed even when the uterus is intact. The first flap 102 and the second flap can be attached inside the patient's body through various attachment elements or means. In some embodiments, the attachment elements include, without limitations, sutures, adhesives, bonding agents, mechanical fasteners (e.g. a medical grade plastic clip), staples, and the like. In some embodiments, the implant 100 can be sutured to bodily tissues with the use of a suturing device such as a Capio™ (as sold and distributed by Boston Scientific Corporation) and the like. In some embodiments, the implant 100 can be delivered inside a patient's body using any suitable insertion tool such as a needle or any other device. In some embodiments, a dilator may be attached to the implant 100 to deliver the implant 100 inside the patient's body.

In various embodiments, as discussed above, the implant 100 is made of a single piece of material. In some embodiments, the material is synthetic. In some embodiments, the implant 100 includes a polymeric mesh body. Exemplary polymeric materials are polypropylene, polyester, polyethylene, nylon, PVC, polystyrene, and the like. In some other embodiments, the implant 100 includes a polymeric planar body without mesh cells. In some embodiments, the implant 100 is made of a mesh body made of a non-woven polymeric material. An example of the mesh, out of which the implant 100 is formed, can be Polyform® Synthetic Mesh developed by the Boston Scientific Corporation. The Polyform® Synthetic Mesh is made from uncoated monofilament macroporous polypropylene. Typically, the surface of the implant 100 is made smooth to avoid/reduce irritation on adjacent body tissues during medical interactions. Additionally, the implant 100 is stretchable and flexible to adapt movements along the anatomy of the human body and reduce suture pullout. Furthermore, softness, lightness, conformity, and strength are certain other attributes that can be provided in the implant 100 for efficient tissue repair and implantation. In some embodiments, the implant 100 can be made of natural materials such as biologic material or a cadaveric tissue and the like. Exemplary biologic materials are bovine dermis, porcine dermis, porcine intestinal sub mucosa, bovine pericardium, a cellulose based product, cadaveric dermis, and the like.

In some embodiments, different portions of the implant may be configured to display or have different biomechanical profiles. For example, in some embodiments portions of the implant may include a coating, such as a silicone coating that may impart or provide elasticity factors to the portions of the implant. The coating may also secure or help prevent the fibers or filaments of the implant from moving with respect to each other. In some embodiments, the coating may be configured to degrade or partially degrade once disposed within the body of the patient. In some embodiments, portions of the implant may be annealed or softened with respect to other portions of the implant. The annealing or softening can be done in patterns to provide or impart anisotropic characteristics. For example, in some embodiments, heat, radiation, or chemicals may be used to anneal or soften portions of the implant.

In some embodiments, some filaments of the implant can be treated with glue or an adhesive or can be welded to an adjacent filament. Such gluing or welding can provide different characteristics to the different portions of the implant. In some embodiments, different materials may be used to form the different portions of the implant. The different materials may be configured to display and provide different characteristics to the different portions of the implant. In some embodiments, the different portions of the implant may include more filaments or more twists or have a different knit or weave pattern.

In some embodiments, the implant includes a reinforcing fiber or a plurality of reinforcing fibers. The reinforcing fiber or fibers may be disposed at specific locations or extend along a particular direction to provide different characteristics to the different portions of the implant.

In some embodiments, the implant includes flat or planar sheets of material. The sheets of material may have different pore quantities or distributions to provide different characteristics at different portions of the implant. In some embodiments, the implant may include laminated materials. For example, a mesh material may be coupled to or otherwise disposed adjacent to a sheet material. Additionally, one sheet material may be coupled to or otherwise disposed adjacent to another sheet material.

In some embodiments, a portion or portions of the implant may be weakened to provide different characteristics to different portions of the implant. For example, in some embodiments, portions of the implants may be notched, scored, grooved or shaved to introduce weakness or to weaken different portions of the implant.

Figure 2:
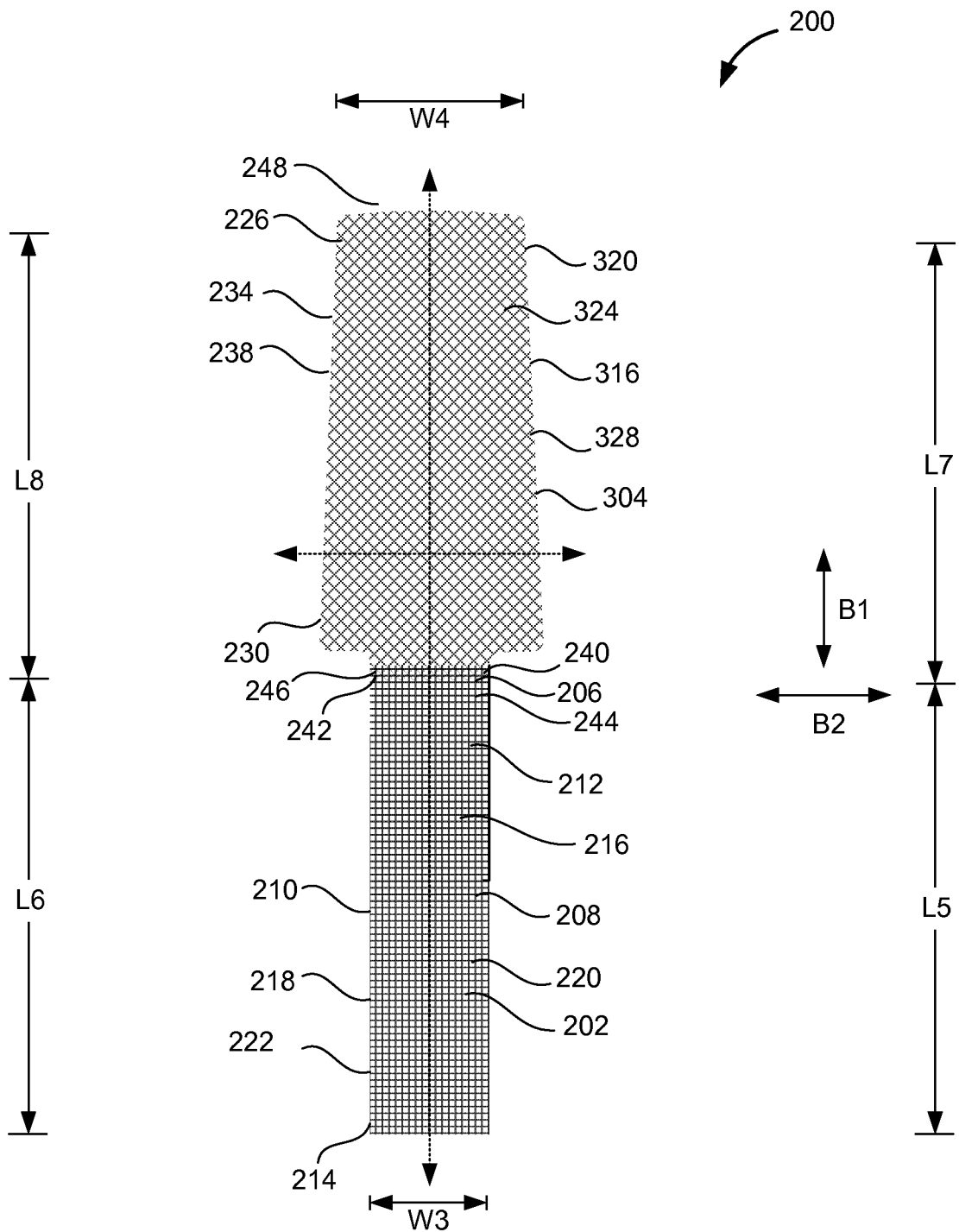
FIG. 2 is a top view of a portion of a medical implant for placing over an anterior vaginal wall and a sacrum inside a patient's body.

FIG. 2 is a perspective view of a first flap 248 of a medical implant 200 for placement over an anterior wall of a vagina inside a patient's body. The first flap 248 can include a first portion 202, a second portion 204 and a transition region 206.

The first portion 202 defines a first side 208, a second side 210, a proximal portion 212 and a distal portion 214. The proximal portion 212 can be attached to or extend from the transition region 206 of the first flap 248. The distal portion 214 can be configured to be attached to a first bodily tissue.

In some embodiments, the first bodily tissue can be a sacrum inside a patient's body. The first portion 202 defines a length L5 along the first side 208 extending from the proximal portion 212 to the distal portion 214. The first portion 202 defines a length L6 along the second side 210 extending from the proximal portion 212 to the distal portion 214. In some embodiments, the length L5 can be equal to the length L6. The first portion 202 defines a width W3 extending between the first side 208 and the second side 210. In some embodiments, the width W3 can remain constant from the proximal portion 212 to the distal portion 214.

In some embodiments, the first flap 248 can be configured so that the first portion 202 can be attached to the sacrum or tissues proximate the sacrum and the remaining portion of the first flap 248 can be attached to the anterior vaginal wall in order to provide support to the anterior vaginal wall.

The first bodily tissue exhibits a definite biomechanical behavior in a defined set of physical conditions. The first portion 202 can be configured to define a set of biomechanical attributes or biomechanical properties so as to emulate the biomechanical behavior of the first bodily tissue, where at least a portion of the first portion 202 is required to be attached, in the defined set of physical conditions. The biomechanical attributes can be defined by a first set of values of respective biomechanical parameters associated with the biomechanical attributes. For example, in some embodiments, the biomechanical attribute can be elasticity and a corresponding biomechanical parameter can be modulus of elasticity, which can be defined by a numerical value. In some embodiments, the biomechanical attribute can be stiffness. In some embodiments, the biomechanical attribute can be strength. In some embodiments, the biomechanical attribute can be resistance to creep. In various embodiments, the biomechanical attributes of the first portion 202 can be defined by defining one or more of shape, size, fabrication method or structure, profile, knit structure, pore size, material of fabrication, and the like. In some embodiments, for example, the congruence between the biomechanical behavior of the first bodily tissue and the first portion 202 can be achieved by varying the shape of the first portion 202. For example, the first portion 202 can have a square, rectangular, triangular or any other shape, which can facilitate the first portion 202 in closely equating the biomechanical behavior of the first bodily tissue.

In some embodiments, the values of the biomechanical attributes of the first portion 202 can be defined by a first type of knit structure 216. In some embodiments, the first type of knit structure 216 can be defined by a first type of knitting pattern 218. In some embodiments, the first type of knit structure 216 can be defined by weaving or knitting the knit with a required and defined tension. For example, the first type of knitting pattern 218 can be woven or knitted tightly or loosely to define a required type of knitting pattern. In some embodiments, the first type of knitting pattern 218 characterized by biomechanical properties of high elastic modulus and stiffness can hold bodily tissue such as a vaginal tissue in the correct anatomical location. In some embodiments, the first type of knit structure 216 can be defined by a first type of pore construct 220. The first type of pore construct 220 includes a plurality of pores 222. The first type of pore construct 220 can be fabricated to define biomechanical attributes conforming to biomechanical behavior of the first bodily tissue by varying the first type knit structure 216, and the pore construct 220. The different ways of achieving the desirable biomechanical attributes for the first portion 202 of the first flap 248 can be used in isolation or in combination. In some embodiments, the knit structure includes knitting, weaving, braiding, twisting, tying, or any combination thereof.

It must be appreciated that though the above ways of defining the required biomechanical attributes are used for mesh-based implants 200 including a knit pattern, the implant 100 can be fabricated as a planar structure. In such embodiments, the biomechanical attributes of the first portion 202 of the first flap 248 can be defined for example by the material used in fabrication of the first portion 202, shape and size of the portion, and the like without limitations. For example, a rigid medical grade polymer can be used for fabricating the first portion 202 thereby defining the biomechanical attribute of rigidity for the first portion 202 to a desired value.

The second portion 204 defines a first side 224, and a second side 226, a proximal portion 228 and a distal portion 230. The distal portion 230 can be attached to or extend from the transition region 206 of the first flap 248. The proximal portion 228 can be configured to be attached to the second bodily tissue. In some embodiments, the second bodily tissue can be an anterior vaginal wall inside a patient's body.

The second portion 204 defines a length L7 along the first side 224 extending from the proximal portion 228 to the distal portion 230. The second portion 204 defines a length L9 along the second side 226 extending from the proximal portion 228 to the distal portion 230. In some embodiments, the length L7 can be different from the length L9. The second portion 204 defines a width W4 extending between the first side 224 and the second side 226. In some embodiments, as illustrated, the width W4 can differ from the proximal portion 228 to the distal portion 230. In some embodiments, the second portion 204 is fabricated such that the width W4 is greater than the width W3 of the first portion 202. In some embodiments, the second portion 204 can define a trapezoidal shape such that the width W4 at the proximal portion 228 is substantially greater than the width W4 at the distal portion. The second portion is configured to be attached and provide support to a second bodily tissue.

The second bodily tissue exhibits a definite biomechanical behavior in a defined set of physical conditions. The behavior exhibited by the second bodily tissue can be different than the behavior exhibited by the first bodily tissue. The second bodily tissue can be configured to define a set of biomechanical attributes or biomechanical properties so as to emulate the biomechanical behavior of the second bodily tissue in the defined set of physical conditions. The biomechanical attributes can be defined by a second set of values of respective biomechanical parameters associated with each of the biomechanical attributes. The second set of values can be different from the first set of values. Consequently, the second portion 204 may be defined to exhibit values of the biomechanical attributes, different than the values of the biomechanical attributes of the first portion 202, in accordance with the second bodily tissue where at least a portion of the second portion 204 of the first flap 248 may be attached. It must be appreciated that in some embodiments, only one or more but not all of the first set of values biomechanical attributes and the second set of values differ in terms of their values of parameters defining the respective attributes. For example, the modulus of elasticity may be same for the first portion 202 and the second portion 204 but any other parameter for other attribute such as resistance to creep may be different. In some other embodiments, all the attributes of the first portion 202 and the second portion 204 may differ in terms of their values of parameters defining the respective attributes. The values of the various parameters provide mathematical measures of the respective parameters.

In some embodiments, the second set of values associated with the biomechanical attributes can be different along different directions for the same fixed set of physical conditions even for the same attribute. For example, in some embodiments, a value of a parameter P defining an attribute T along a first direction B1 can be different from a value of the parameter P defining the attribute T along a second direction B2. In some embodiments, the first direction B1 can be a longitudinal direction and the second direction B2 can be a transverse direction. Therefore, a parameter may differ in its value in different directions, in some embodiments. For example, modulus of elasticity of various portions of the first flap 248 may differ in different directions, in some embodiments. This may be important to match the biomechanical behavior of bodily tissues that may exhibit different levels of elasticity in different directions. Also, the second set of values associated with the biomechanical attributes can vary with a variation in the set of physical conditions. However, in some embodiments, the physical conditions may vary and measurement of the biomechanical behavior and the attributes may accordingly be calibrated so as to compare the various values associated with the various attributes in light of the required characteristics at the required locations. In some embodiments, the first direction B1 and the second direction B2 do not align along the axes of the implant. Additionally, in some embodiments, B1 and B2 are not disposed orthogonal or perpendicular to one another.

In some embodiments, the biomechanical attributes can include elasticity and a corresponding biomechanical parameter can be modulus of elasticity. In some embodiments, the biomechanical attribute can be viscoelasticity. In some embodiments, the biomechanical attribute can be viscohyperelasticity. In some embodiments, the biomechanical attribute can be anisotropicity. In various embodiments, the biomechanical attributes of the second portion 204 can be defined by defining one or more of shape, size, fabrication method or structure, profile, knit structure, pore size, material of fabrication, and the like. In some embodiments, for example, the congruence between the biomechanical behavior of the second bodily tissue and the second portion 204 can be achieved by varying the shape of the second portion 204. For example, the trapezoidal shape of the second portion 204 can conform to the shape of the second bodily tissue such as the anterior vaginal wall. The trapezoidal shape can be provided to the second portion 204 to emulate a taper of an outer vaginal canal. In some embodiments, at the widest end, the width W4 can range from 21.7-55 mm. In some embodiments, at the narrowest end, the width W4 can range from 18.7-37 mm. The lengths L6 or L8 of the trapezoid can range from 40.8-95 mm based on the linear length of the vagina.

In some embodiments, the values of the biomechanical attributes of the second portion 204 can be defined by a second type of knit structure 232. In some embodiments, the second type of knit structure can be defined by a second type of knitting pattern 234. In some embodiments, the second type of knit structure 232 can be defined by weaving the knit with a required and defined tension. For example, the anterior vaginal wall shows anisotropic behavior, with biasness toward more elongation along a transverse direction such as the direction B1, therefore, the second type of knitting pattern 234 can be selected so as to be more elastic along a longitudinal direction such as the direction B2 as compared to the transverse direction.

In some embodiments, the second type of knit structure 232 can be defined by a second type of pore construct 236. In some embodiments, the second type of pore construct 236 is different from the first type of pore construct 220. The second type of pore construct 236 includes a plurality of pores 238. In some embodiments, the difference in pore construct for the first portion 202 and the second portion 204 can be achieved by weaving or knitting a mesh with different pore sizes. In some embodiments, the difference in pore constructs 220 and 236 of the first portion 202 and the second portion 204 can be achieved by extruding or knitting a single pore size mesh and heat setting the pores to set a different pore size for the first portion 202 and the second portion 204 as illustrated and described by later figures. The second pore construct 236 can define the second set of values of the biomechanical attributes of the second portion 204. In an embodiment, the second pore construct 236 can define larger pore sizes as compared to the remaining portion of the first flap 248. In some embodiments, the second pore construct 236 can be fabricated to exhibit biomechanical attributes of high flexibility and elongation to a particular strain level and high stiffness after a particular stain level is reached. Such a strain behavior closely emulates the biomechanical behavior of the anterior vaginal wall.

In some embodiments, one or more of the biomechanical attributes can be defined by a material used for fabricating the second portion 204. For example, a viscoelastic medical grade polymer can be used for fabricating the second portion 204 thereby defining a value for the biomechanical attribute of viscoelasticity for the second portion 204. In some embodiments, an anisotropic medical grade polymer can be used for achieving a desired value of anisotropicity. In some embodiments, the desired value of ansiotropicity may be achieved though the process of forming the device or portion of the device. In some embodiments, a creep resistant medical grade polymer can be used for achieving a desired value of creep resistance.

Generally, the anterior vaginal wall can be viscohyperelastic. The second portion therefore can be defined such that it exhibits high viscoelasticity. In some embodiments, the biomechanical parameters can have different values in different directions. For example, the biomechanical parameters may have different values in the first direction B1 than in the second direction B2.

The values of the biomechanical parameters defining the biomechanical behavior of the anterior vaginal wall may vary under different load conditions. For example, in some embodiments, the stiffness of the anterior vaginal wall at a low strain along the direction B1 can range from 0.431-4.15 MegaPascal (MPa). In some embodiments, the stiffness of the anterior vaginal wall at a high strain along the direction B1 can range from 5.15-17.28 MPa. In some embodiments, the stiffness the anterior vaginal wall at the low strain along the direction B2 can range from 0.385-0.415 MPa. In some embodiments, the stiffness of the anterior vaginal wall along the direction B2 at the high strain can range from 0.370-0.61 MPa. The stiffness behaviors of the anterior vaginal wall are further explained in detail in conjunction with FIGS. 6A and 6B. Therefore, in some embodiments, the second portion 204 of the first flap 248 can be fabricated so as to define a set of values of the biomechanical parameter of stiffness that can conform to the values defining the biomechanical behavior of the anterior vaginal wall under similar load conditions.

The first flap 248 further includes the transition region 206 as mentioned above. The transition region 206 defines a proximal portion 240 and a distal portion 242. The proximal portion 240 can be coupled to or extend from the distal portion 230 of the second portion 204. The distal portion 242 can be coupled to or extend from the proximal portion 212 of the first portion 202. In some embodiments, the transition region 206 may define a third type of knit structure 244 that monolithically joins the first portion 202 and the second portion 204. In some embodiments, the third knit structure 244 may define a third type of pore construct 246. In some embodiments, the first flap 248 can be formed by suturing together the first portion 202 and the second portion 204. In such cases, the transition region 206 includes sutures tying the first portion 202 and the second portion 204.

Figure 3:
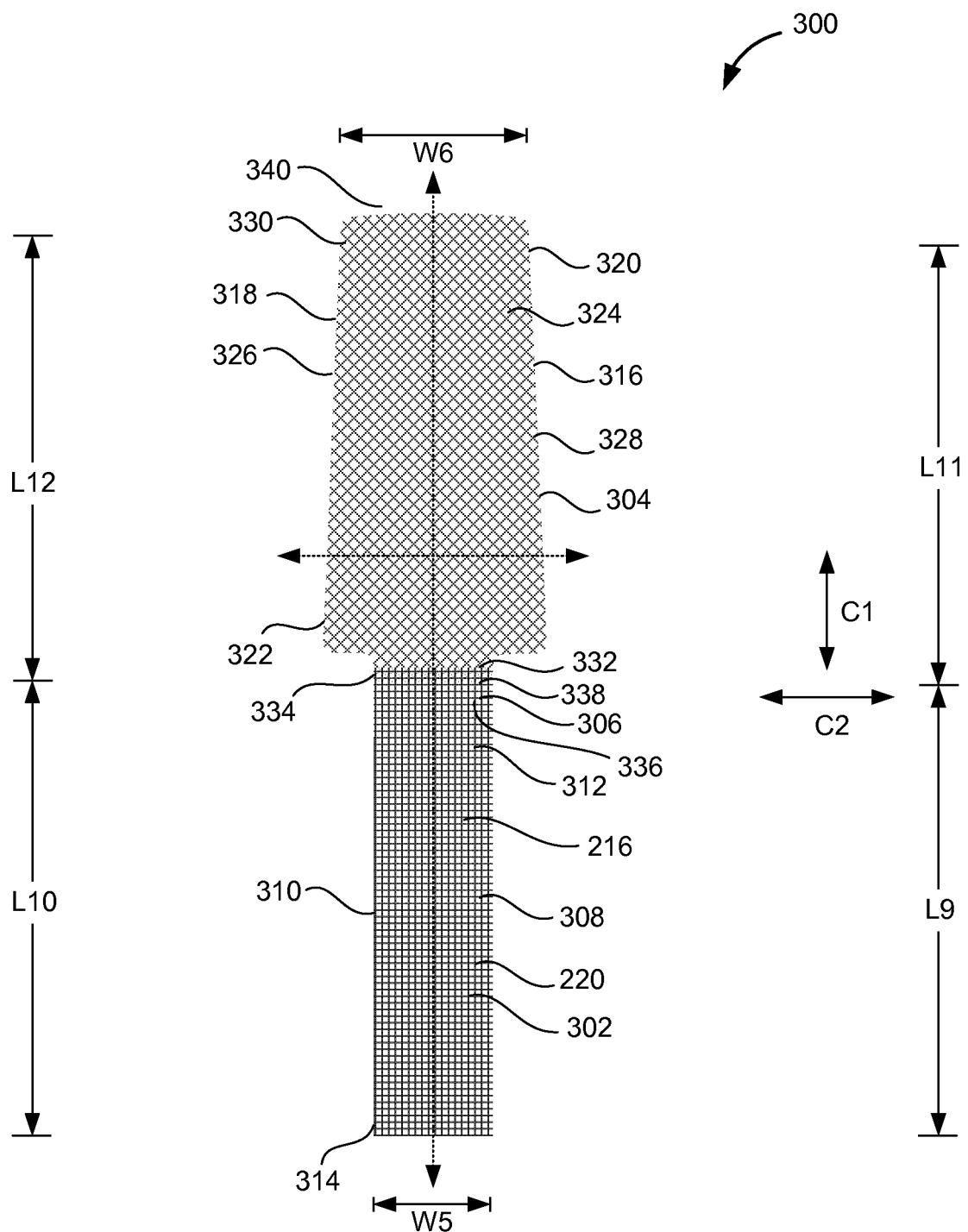
FIG. 3 is a top view of a portion of a medical implant for placing over a posterior wall of a vagina and a sacrum inside a patient's body.

FIG. 3 is a perspective view of a second flap 340 of the medical device 200 for placement over a posterior wall of a vagina inside a patient's body. The first flap 248 and the second flap 340 can collectively form the medical implant 200. The second flap 340 can include a first portion 302, a second portion 304 and a transition region 306.

The first portion 302 defines a first side 308, a second side 310, a proximal portion 312 and a distal portion 314. The proximal portion 312 can be attached to or extend from the transition region 306 of the second flap 340. The distal portion 314 can be configured to be attached to a first bodily tissue. In some embodiments, the first bodily tissue can be a sacrum or tissues proximate the sacrum. The first portion 302 defines a length L9 along the first side 308 extending from the proximal portion 312 to the distal portion 314. The first portion 302 defines a length L10 along the second side 310 extending from the proximal portion 312 to the distal portion 314. In some embodiments, the length L9 can be equal to the length L10. The first portion 302 defines a width W5 extending between the first side 308 and the second side 310. In some embodiments, the width W5 can remain constant from the proximal portion 312 to the distal portion 314.

In some embodiments, the second flap 340 can be configured so that the first portion 302 can be attached to the sacrum and the remaining portion of the implant 300 can be attached to the posterior vaginal wall in order to provide support to the posterior vaginal wall. The first bodily tissue exhibits a definite biomechanical behavior in a defined set of physical conditions. The first portion 302 can be configured to define a set of biomechanical attributes or biomechanical properties so as to emulate the biomechanical behavior of the first bodily tissue, where at least a portion of the first portion 302 is required to be attached, in the defined set of physical conditions. The first portion 302 of the second flap 340 can be fabricated similar to the first portion 202 of the first flap 248 as described in FIG. 2. The attributes of the first portion 302 of the second flap 340 can be defined in a manner similar to the attributes of the first portion 202 of the first flap 248.

The second portion 304 defines a first side 316, and a second side 318, a proximal portion 320 and a distal portion 322. The distal portion 322 can be attached to or extend from the transition region 306 of the second flap 340. The proximal portion 320 can be configured to be attached to a third bodily tissue. In some embodiments, the third bodily tissue can be the posterior vaginal wall.

The second portion 304 defines a length L11 along the first side 316 extending from the proximal portion 320 to the distal portion 322. The second portion 304 defines a length L12 along the second side 318 extending from the proximal portion 320 to the distal portion 322. In some embodiments, the length L11 can be different from the length L12. The second portion 304 defines a width W6 extending between the first side 316 and the second side 318. In some embodiments, as illustrated, the width W6 can differ from the proximal portion 320 to the distal portion 322. In some embodiments, the second portion 304 is fabricated such that the width W6 is greater than the width W5 of the first portion 302. In some embodiments, the second portion 304 can define a trapezoidal shape such that the width W6 at the proximal portion 320 is substantially greater than the width W6 at the distal portion 322.

The third bodily tissue exhibits a definite biomechanical behavior in a defined set of physical conditions. The behavior exhibited by the third bodily tissue can be different than the behavior exhibited by the first bodily tissue or the second bodily tissue. The third bodily tissue can be configured to define the biomechanical attributes or biomechanical properties so as to emulate the biomechanical behavior of the third bodily tissue in the defined set of physical conditions. The biomechanical attributes can be defined by a third set of values of respective biomechanical parameters associated with the biomechanical attributes. In some embodiments, the third set of values can be different from the first set of values of the biomechanical attributes. In some embodiments, the third set of values can be different from the second set of values of the biomechanical attributes. Consequently, the second portion 304 may be defined to exhibit biomechanical attributes, different than the biomechanical attributes of the first portion 302, in accordance with the third bodily tissue where at least a portion of the second portion 304 may be attached. The second portion 304 may be defined to exhibit biomechanical attributes, different than the biomechanical attributes of the first portion 202 from the first flap 248.

In some embodiments, the third set of values associated with the biomechanical attributes can be different along different directions for the same fixed set of physical conditions even for the same attribute. For example, in some embodiments, a value of a parameter P defining an attribute T along a first direction C1 can be different from a value of the parameter P defining the attribute T along a second direction C2. In some embodiments, the first direction C1 can be a longitudinal direction and the second direction C2 can be a transverse direction. Also, the third set of values associated with the biomechanical attributes can vary with a variation in the set of physical conditions. In some embodiments, the third set of values can be different from the first set of values associated with the biomechanical attributes under the same fixed set of physical conditions.

In some embodiments, the biomechanical attribute can include elasticity and a corresponding biomechanical parameter can be modulus of elasticity. In some embodiments, the biomechanical attribute can be viscoelasticity. In some embodiments, the biomechanical attribute can be viscohyperelasticity. In some embodiments, the biomechanical attribute can be anisotropicity. In various embodiments, the biomechanical attributes of the second portion 304 can be defined by defining one or more of shape, size, fabrication method or structure, profile, knit structure, pore size, material of fabrication, and the like. In some embodiments, for example, the congruence between the biomechanical behavior of the third bodily tissue and the second portion 304 can be achieved by varying the shape of the second portion 304. For example, the trapezoidal shape of the second portion 304 can conform to shape of the posterior vaginal wall.

In some embodiments, the values of the biomechanical attributes of the second portion 304 can be defined by a fourth type of knit structure 324. In some embodiments, the fourth type of knit structure 324 can be defined by a fourth type of knitting pattern 326. In some embodiments, the fourth type of knit structure 324 can be defined by weaving the knit with a required and defined tension. For example, the posterior vaginal wall shows biomechanical behavior of anisotrophicity, with biasness (or being biased) toward more elongation along the direction C1, therefore, the fourth type of knitting pattern 326 can be selected to be more elastic along the direction C2 as compared to the direction C1.

In some embodiments, the fourth type of knit structure 324 can be defined by a fourth type of pore construct 328. In some embodiments, the fourth type of pore construct 328 is different from the first type of pore construct 220 and the second type of pore construct 236 of FIG. 2. The fourth type of pore construct 328 includes a plurality of pores 330. The difference in pore construct for the first portion 302 and the second portion 304 can be achieved as described in FIG. 2. The fourth type of pore construct 328 can be configured to conform to biomechanical properties of the posterior vaginal wall.

In some embodiments, one or more of the biomechanical attributes can be defined by the third set of values associated with the biomechanical attributes for the second portion 304. In an embodiment, the third set of values may be defined by a material used for fabricating the second portion 304. For example, a viscoelastic medical grade polymer can be used for fabricating the second portion 304 thereby defining a desired value of viscoelasticity for the second portion 304. In some embodiments, an anisotropic medical grade polymer can be used for achieving a desired value of anisotropicity. In some embodiments, the device is formed such that it has the desired value of anisotropicity is achieved. In some embodiments, a creep resistant medical grade polymer can be used for achieving a desired value of creep resistance.

The posterior vaginal wall can have high visco-hyperelasticity. Therefore, the second portion 304 can have a high value of viscohyperelasticity under a fixed set of stress conditions. In some embodiments, the value of the biomechanical parameter can be different for the first direction C1 and the second direction C2 for the posterior vaginal wall. The value of the biomechanical parameter would be different for a set of high load conditions and a set of low load conditions for the posterior vaginal wall. For example, in some embodiments, the stiffness of the posterior vaginal wall at a low strain along the direction C1 can range from 0.46-0.98 MegaPascal (MPa). In some embodiments, the stiffness of the posterior vaginal wall at a high strain along the direction C1 can range from 2.49-9.08 MPa. In some embodiments, the stiffness of the posterior vaginal wall at the low strain along the direction C2 can range from 1.14-1.46 MPa. In some embodiments, the stiffness of the posterior vaginal wall along the direction C2 at the high strain can range from 2.39-3.83 MPa. These values indicate an anisotropic behavior and stiffness variation along different directions and different physical conditions for posterior vaginal wall. The stiffness behaviors of the posterior vaginal wall are explained in detail by FIGS. 6A and 6B. Therefore, in some embodiments, the second portion 304 of the second flap 340 can be fabricated so as to define a set of values of the biomechanical parameter of stiffness that can conform to the values defining the biomechanical behavior of the posterior vaginal wall under similar load conditions. The second portion 304 can be fabricated such that the set of values of the biomechanical parameter can be different from the set of values for the same biomechanical parameter of the second portion 204 of the first flap 248.

The second flap 340 further includes the transition region 306 as mentioned above. The transition region 306 defines a proximal portion 332 and a distal portion 334. The proximal portion 332 can be coupled to or extend from the distal portion 322 of the second portion 304. The distal portion 334 can be coupled to or extend from the proximal portion 312 of the first portion 302. In some embodiments, the transition region 306 defines a fifth type of knit structure 336 that monolithically joins the first portion 302 and the second portion 304. The fifth type of knit structure 336 defines a fifth pore construct 338. In some embodiments, the third knit structure 244 may define a third type of pore construct 246.

In some embodiments, the second flap 340 can be made out of a single strip of material. In some embodiments, the second flap 340 can be formed by suturing together the first portion 302 and the second portion 304. In such cases, the transition region 306 includes sutures tying the first portion 302 and the second portion 304.

Figure 4:
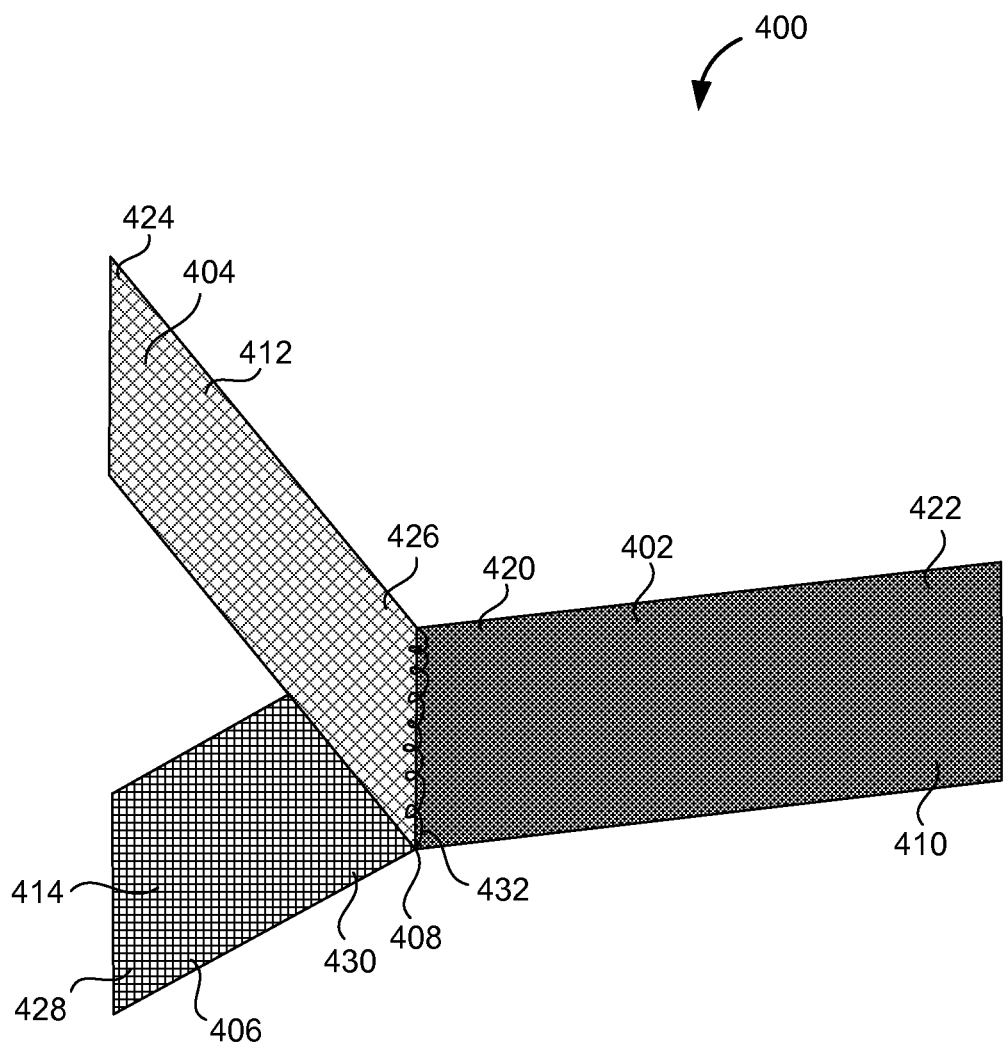
FIG. 4 is a perspective view of a medical implant including multiple flaps for placing over an anterior vaginal wall, a posterior vaginal wall, and a sacrum, in an embodiment of the present invention.

FIG. 4 is a perspective view of a medical implant 400 including a plurality of flaps for placement over the first bodily tissue, the second bodily tissue and the third bodily tissue inside a patient's body. The plurality of flaps may include a first flap 402, a second flap 404, and a third flap 406. The plurality of flaps can be joined together at a transition region 408 to form a Y-shaped implant as illustrated in the FIG. 4. In some embodiments, there may not be any transition regions such as the transition region 408 and the first, second, and third flaps can directly be coupled with the use of sutures or any other coupler.

The first flap 402 defines a proximal portion 420 and a distal portion 422. The proximal portion 420 can be attached to or extend from the transition region 408 of the medical implant 400. The distal portion 422 can be configured to be attached to the first bodily tissue as described with reference to FIG. 2. The first flap 402 can be configured to define the first set of values corresponding to the biomechanical parameters as explained in FIG. 2 for emulating biomechanical behavior of first bodily tissue for example the sacrum, or tissue proximate the sacrum.

The second flap 404 defines a proximal portion 424 and a distal portion 426. The proximal portion 424 can be attached to or extend from the transition region 408 of the medical implant 400. The distal portion 426 can be configured to be attached to the second bodily tissue as described with reference to FIG. 2. The second flap 404 can be configured to define the second set of values corresponding to the biomechanical parameters as explained in FIG. 2 for emulating biomechanical behavior of the second bodily tissue for example, the anterior vaginal wall.

The third flap 406 defines a proximal portion 428 and a distal portion 430. The proximal portion 428 can be attached to or extend from the transition region 408 of the medical implant 400. The distal portion 430 can be configured to be attached to the third bodily tissue as described with reference to FIG. 3. The third flap 406 can be configured to define the third set of values corresponding to the biomechanical parameters as explained in FIG. 3 for emulating biomechanical behavior of third bodily tissue, for example, the posterior vaginal wall.

In some embodiments, the first flap 402, the second flap 404 and third flap 406 can be fabricated independent of each other. The first flap 402, the second flap 404 and the third flap 406 can be tied together with a suture 432 at the transition region 408 to form the medical implant 400. In some embodiments, the three flaps 402, 404, and 406 exhibit different biomechanical attributes owning to different biomechanical properties of anatomical locations that each of the three flaps 402, 404, and 406 are configured to be attached to.

As mentioned above, the biomechanical properties of the posterior wall of vagina, the anterior wall of vagina and the sacrum or tissues proximate the sacrum inside a patient's body are different from each other; therefore in some embodiments the flaps of the medical implant 400 are fabricated with a pore construct and knit structure that can closely mimic biomechanical attributes of the anatomical locations inside the patient's body. For example, the first flap 402 can have a knit structure 410 similar to the first knit structure 216 of the first portion 202 of the first flap 248 from FIG. 2 so as to be biomechanically congruent with the first bodily tissue. The second flap 404 can have a knit structure 412 similar to the second knit structure 232 of the second portion 204 of the first flap 248 from FIG. 2 so as to be biomechanically congruent with the second bodily tissue. The third flap 406 can have a knit structure 414 similar to the fourth knit structure 324 of the second flap 340 from FIG. 3 so as to be biomechanically congruent with the third bodily tissue. Upon placement, the first flap 402, the second flap 404, and the third flap 406 can act as three different arms that can be configured to support the pelvic organs like the anterior vaginal wall, the posterior vaginal wall and the sacrum by attaching the implant 400 at three distinct bodily locations. The three arms can be movable with respect to one another to conform to the shape of the target anatomical location of attachment inside the body. The three arms can take a shape such as linear/planar, curvilinear, curved, or any other shape.

In some embodiments, for example, the medical implant 400 can be formed by tying together the second portion 204 of the first flap 248, the second portion 304 of the second flap 340 and the first portion 202 or 302 from either the first flap 348 or the second flap 340. In such cases, the three portions mentioned above conform to the biomechanical attributes of the second bodily tissue, the third bodily tissue and the first bodily tissue respectively.

Figure 5A:
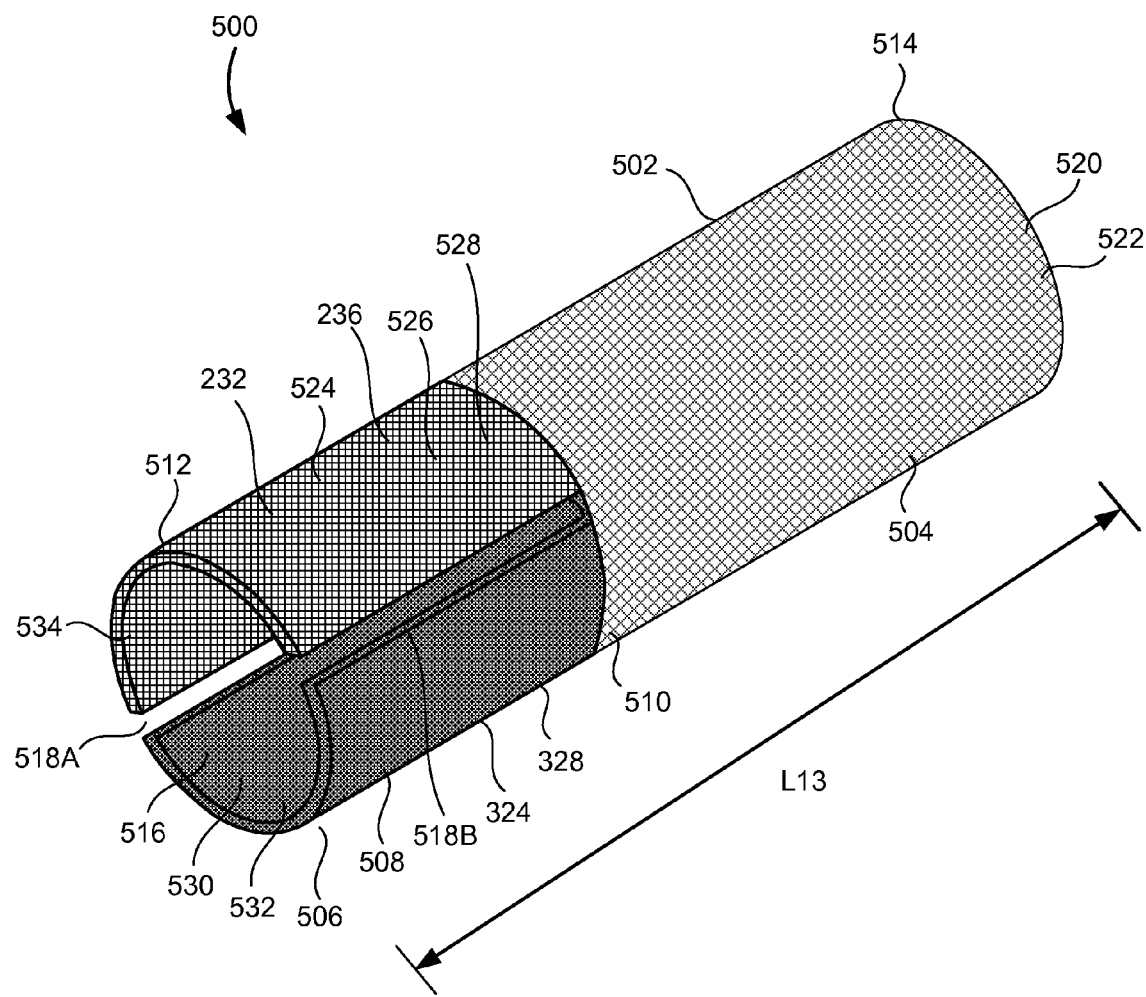
FIG. 5A is a perspective view of a tubular shaped medical implant including portions to be attached to a sacrum or proximate the sacrum, an anterior vaginal wall and a posterior vaginal wall in an embodiment of the invention.

FIG. 5A is a perspective view of a medical implant 500 formed as a tubular structure 502.

The tubular structure 502 of the medical implant includes a first portion 504, a second portion 506, and a transition region 510. The transition region 510 is formed from intersection of the first, and the second 504, and 506 of the tubular structure 502 of the medical implant 500. The medical implant 500 defines a proximal portion 512, a distal portion 514 and a lumen 516 extending from the proximal portion 512 to the distal portion 214. The medical implant 500 defines a length L13 from the proximal portion 512 to the distal portion 514. The medical implant includes the second portion 506 at the proximal portion 512 of the medical implant. The second portion can a first section 524 and a second section 508 and two slits 518A and 518B extending laterally along the length L13 of the medical implant 500. In some embodiments, the proximal portion 512 includes two slits extending laterally along the length L13 and into the lumen 516 of the medical implant 500. The slits 518A and 518B can configure first section 524 as apart from the second section 508 at a proximal end 534 of the medical implant 500. The medical implant 500 can be configured so that each of the first portion 504, the first section 524 and the second section 508 can define a set of biomechanical attributes, which can be congruent with the sacrum or tissues proximate the sacrum, the anterior vaginal wall and the posterior vaginal wall respectively. The congruency can be achieved by any of the methods described with reference to FIGS. 2-3.

The first portion 504 can define a knit structure 520 formed of a pore construct 522. In some embodiments, the pore construct 522 can define a pore size so as to accommodate values of the biomechanical attributes the first bodily tissue. The first section 524 can define a knit structure 526 formed of a pore construct 528. In some embodiments, the pore construct 528 can define a pore size so as to accommodate values of the biomechanical attributes the second bodily tissue. The second section 508 can define a knit structure 530 formed of a pore construct 532. In some embodiments, the pore construct 532 can define a pore size so as to accommodate values of the biomechanical attributes the third bodily tissue. In some embodiments, the knit structure 520 of the first portion 504 is different from the knit structure 526 and the knit structure 530 of the first section 524 and the second section 508 of the second portion 506. In some embodiments, the knit structure 526 of the first section 524 is different from the knit structure 530 of the second section 508.

In some embodiments, the first portion 504 can be configured for attaching to the sacrum, the first section 524 to the anterior vaginal wall and the second section 508 to the posterior vaginal wall. In some embodiments, a value corresponding to a biomechanical parameter defining a biomechanical attribute of the first section 524 attaching to the anterior vaginal wall is different from a value of the same biomechanical parameter of the second section 508 attaching to the posterior vaginal wall. For example, the value of elasticity can be different for the first section 524 and the second section 508 under similar strain conditions.

Figure 5B:
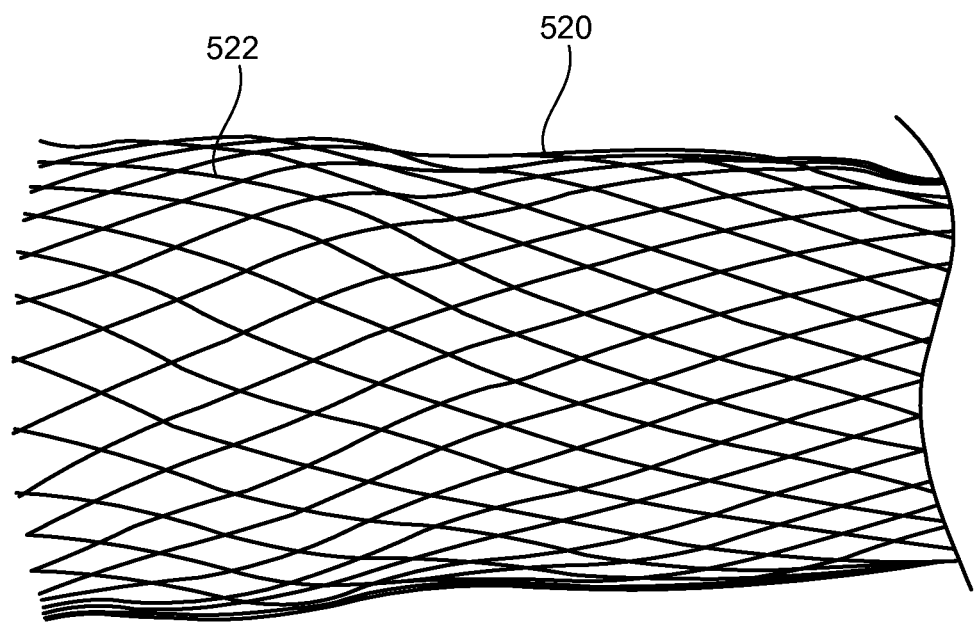
FIG. 5B is a perspective view of a portion of the tubular shaped medical implant with a pore construct in a closed position, in accordance with an embodiment of the invention.
Figure 5C:
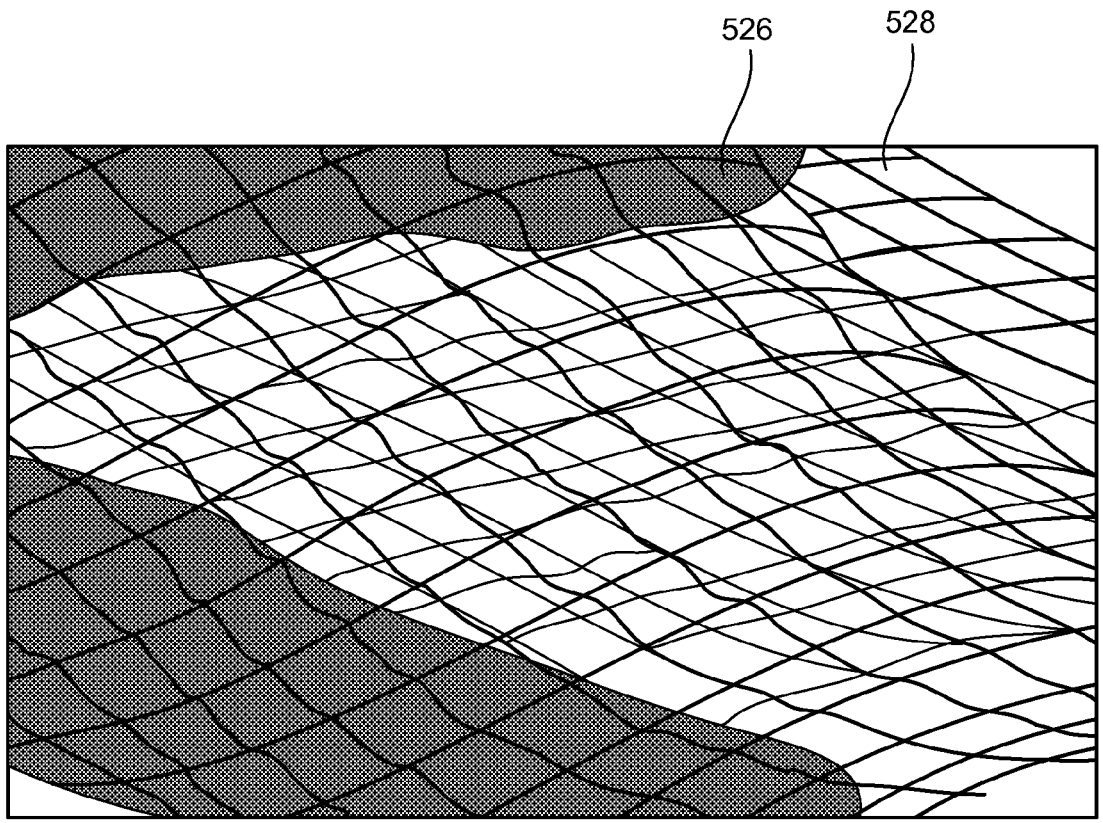
FIG. 5C is a perspective view of the tubular shaped medical implant with the pore construct in a closed position, in accordance with an embodiment of the invention.

In some embodiments, the medical implant 500 can be formed from a process of extrusion. The pore constructs 522, 528, and 532, in such cases can be the same. The medical implant can then be provided a heat treatment and different portions of the medical implant 500 can be heat set to different pore sizes. For example, the pore construct 522 can remain in a closed position without application of heat as illustrated in FIG. 5B. The second portion 506 can be manually stretched to bring the medical implant 500 in an open position as illustrated in FIG. 5C. This can increase a pore size of the pore constructs 528 and 532. The pore construct 528 and the pore construct 532 can remain in an open position on application of heat over the first section 524 and the second section 508. The first section 524 and the second section 508 may each be given heat treatment for setting different pore sizes so as to facilitate defining biomechanical attributes emulating biomechanical behavior of the anterior and posterior vaginal walls respectively.

In some embodiments, the medical implant 500 can be fabricated so that the first portion 504 includes the knit structure 216 and the pore construct 220 as described for the first flap 248, the second portion 506 includes the knit structure 232 and the pore construct 236 as described for the first flap 248 and the third portion 508 includes the knit structure 324 and the pore construct 328 as described for the second flap 340.

Figure 5D:
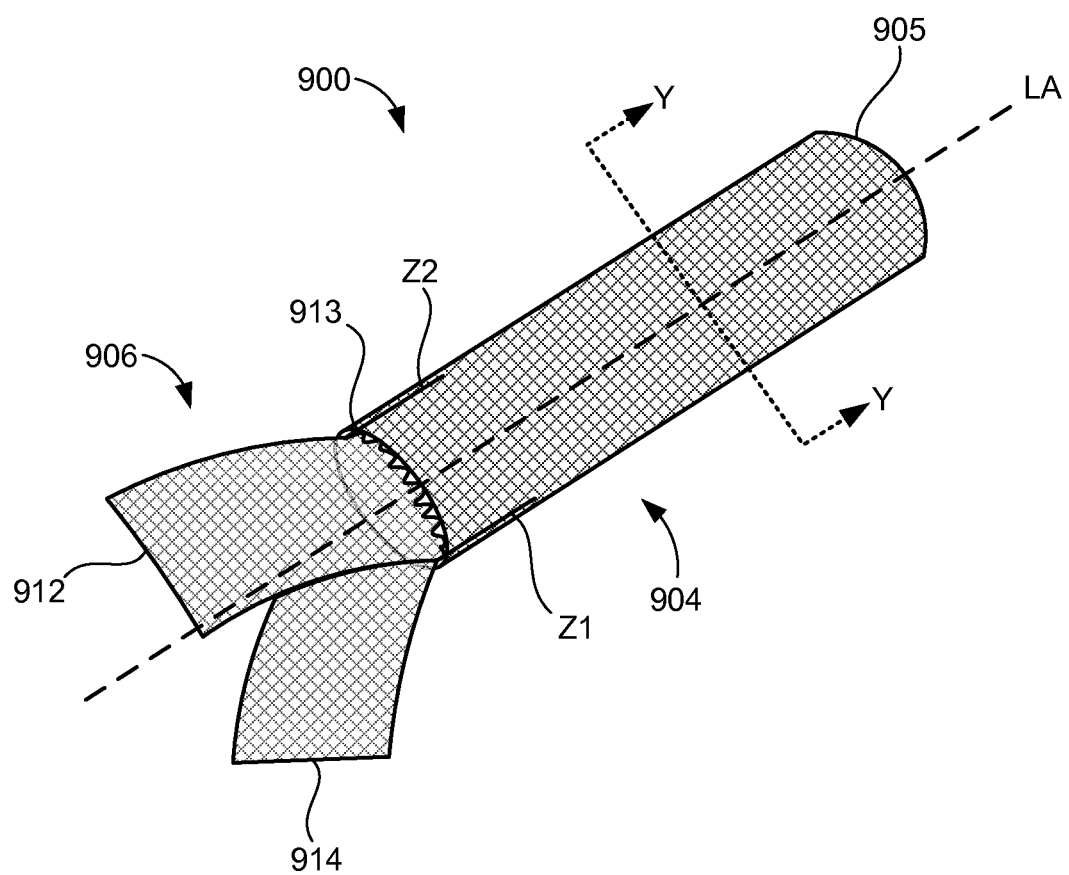
FIG. 5D is a perspective view of a medical implant according to an embodiment of the invention.
Figure 5E:
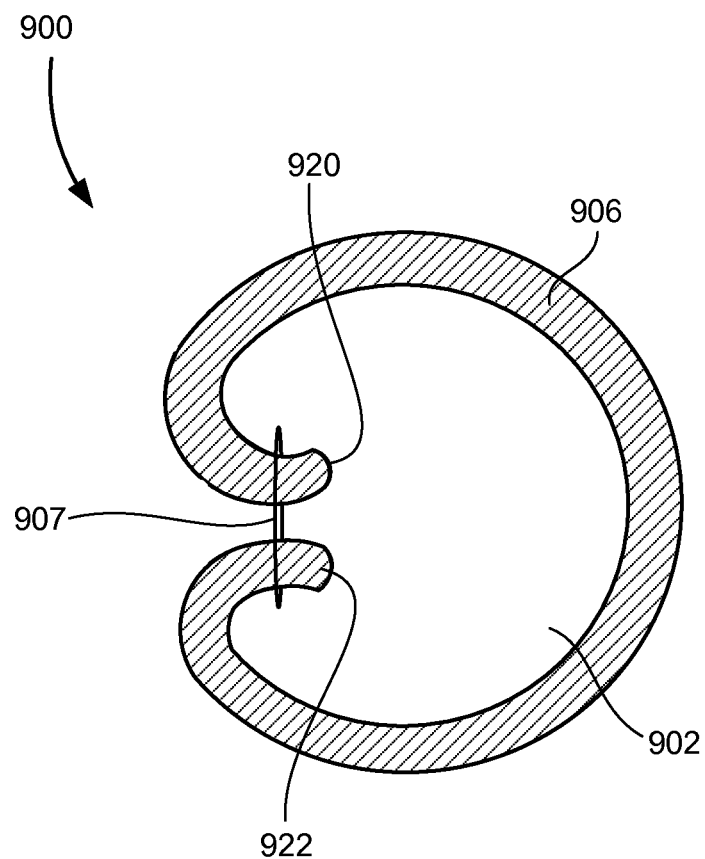
FIG. 5E is a cross-sectional view of the medical implant of FIG. 5D taken along line Y-Y of FIG. 5D.
Figure 5F:
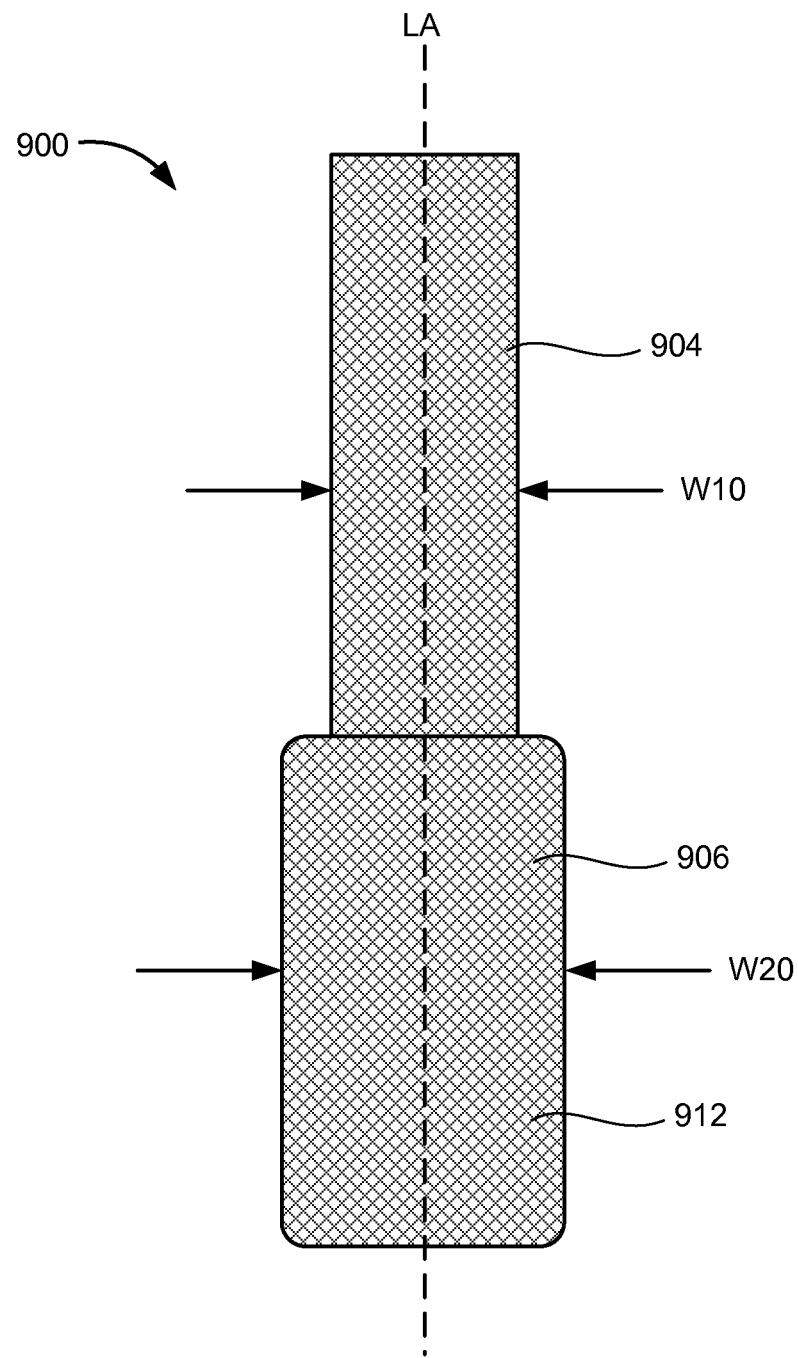
FIG. 5F is a top view of the medical implant of FIG. 5D.

FIG. 5D is a perspective view of a medical implant or medical device 900 according to an embodiment of the invention. FIG. 5E is a cross sectional view of the medical implant 900 taken along line Y-Y of FIG. 5D. FIG. 5F is a top view of the medical implant 900.

In some embodiments, the medical implant or medical device 900 is configured to be placed within a body of a patient and configured to provide support to a portion of the body of the patient, such as a vagina of the patient. In some embodiments, the medical device 900 is configured to be placed or implanted within a body of a patient via an abdominal incision. In other embodiments, the medical implant 900 may be placed or implanted within the body of the patient via another incision or opening such as a vaginal incision.

The medical implant 900 includes a first portion 904 and a second portion 906. In some embodiments, the first portion 904 is configured to be attached to a sacrum of a patient or to a location proximate the sacrum of the patient. For example, an end portion 905 may be configured to be coupled or attached to the sacrum of the patient. The end portion 905 may be coupled or attached to the sacrum via any type of coupling methods, such as via a suture, an anchor, or an adhesive. Alternatively, the end portion 905 of the implant 900 may be passed through the coupling tissue to anchor or couple the medical implant 900 to or near the sacrum of the patient. In other embodiments, the first portion 904 is configured to be coupled or attached to another anchoring portion within the body of the patient.

The second portion 906 of the medical implant 900 includes a first flap 912 and a second flap 914. In some embodiments, the first flap 912 may be coupled or attached to an anterior vaginal wall of the patient. For example, the first flap 912 may be sutured or coupled via another coupling mechanism, such as an anchor or an adhesive, to the anterior vaginal wall of the patient. In some embodiments, the second flap 914 may be coupled or attached to a posterior vaginal wall of the patient. For example, the second flap 914 may be sutured or coupled via another coupling mechanism, such as an anchor or an adhesive, to the posterior vaginal wall. In other embodiments, the first flap 912 and the second flap 914 may be coupled to other portions of the body of the patient.

As best illustrated in FIG. 5E, the first portion 904 of the implant 900 has a tubular structure. Specifically, in the illustrated embodiment, the first portion 904 defines a lumen 902. While the first portion 904 is shown as forming a circular or oval cross sectional shape, in other embodiments, the first portion 904 forms other shapes, such as a flattened oval shape.

The second portion 906 of the implant 900 is coupled to and extends from the first portion 904. Specifically, the first flap 912 of the second portion 906 is coupled to and extends from the first portion 904. In some embodiments, the first flap 912 is stitched to the first portion 904 (or coupled to the first portion 904 via suture 913). In other embodiments, the first flap 912 is coupled to the first portion 904 via another coupling mechanism, such as an adhesive or a coupler. The second flap 914 is coupled to and extends from the first portion 904. In some embodiments, the second flap 914 is stitched to the first portion 904. In other embodiments, the second flap 914 is coupled to the first portion 904 via another coupling mechanism, such as an adhesive or a coupler.

In some embodiments, the first portion 904 behaves differently in the body of the patient than the second portion 906. For example, in some embodiments, the first portion 904 has a value corresponding to a biomechanical parameter defining a biomechanical attribute that differs from a value corresponding to a value of the biomechanical parameter defining the biomechanical attribute of the second portion 906. For example, in some embodiments, the first portion 904 is stiffer or less flexible than the second portion 906. In such embodiments, the second portion 906 is more flexible or more compliant than the first portion 904. Specifically, the first flap 912 of the second flap 914 are more flexible or more compliant (and less stiff) than the first portion 904. In some embodiments, first flap 912 may be more or less flexible than the second flap 914. As the first flap 912 and the second flap 914 are flexible, in some embodiments, they may be configured to assume the flexibility or elasticity of the vaginal walls to which they are attached. As the first portion 904 is more stiff (less flexible), in some embodiments, the first portion 904 is configured to provide support to the body portions of the patient without flexing or stretching (or without a substantial amount of flexing or stretching).

In some embodiments, the first portion 904 is formed of a mesh material. The mesh material may be a woven or knitted mesh material. In some embodiments, the first portion 904 of the mesh material may be formed as a tubular structure. In other words, the tubular structure may be devoid of a seam. In other embodiments, the mesh material may be formed as a planar or substantially planar sheet and may be placed in a tubular form by coupling one side of the mesh material to another side of the mesh material. The sides or edges of the mesh material may be coupled together via stitching, a heat seal, an ultrasonic weld, or any other coupling mechanism. Sides or edges of mesh materials may be rough or have projecting fibers. In some embodiments, the sides or edges of the mesh material of the first portion 904 may be coupled together such that the rough portions of the sides or edges are not exposed (or on the outer surface of the first portion 904. For example, as best illustrated in FIG. 5E, the sides or edges may be coupled via a suture or a coupler 907 such that the edges are disposed towards or within the lumen 902 defined by the first portion 904. In such embodiments, the first portion 904 may provide increased comfort to the patient as the bodily tissues of the patient may not be exposed to the rough surfaces 920 and 922 of the sides or edges of the mesh of the first portion 904. For example, in some embodiments, without the rough surfaces of the edges being exposed, the first portion 904 is prevented from (or is less likely to) damaging bodily tissue or organs that contact the first portion 904.

In other embodiments, the first portion 904 is formed of any other biocompatible material, such as a biocompatible synthetic material or a natural material.

In some embodiments, the first flap 912 and the second flap 914 are formed of a mesh material. The mesh material may be a woven or knitted mesh material. In some embodiments, the mesh material may be formed as a planar or substantially planar sheet. In other embodiments, the first flap 912 and the second flap 914 may be formed of any other biocompatible material, such as a biocompatible synthetic material or a natural material.

As best illustrated in FIG. 5F, in the illustrated embodiment, the first portion 904 of the implant 900 has a width W10 and the second portion 906 has a width W20. The width is defined as the size or length transverse to the longitudinal axis LA of the device. In the illustrated embodiment, the width W10 of the first portion 904 is less than the width W20 of the second portion 906. For example, in some embodiments the width W10 of the first portion 904 is between 1 and 13 centimeters and the width W20 of the second portion 906 is between 1 and 13 centimeters. In some embodiments, the width of the first flap 912 is the same as the width of the second flap 914. In other embodiments, the width W10 of the first portion 904 is the same as the width W20 of the second portion 906. In some embodiments, the width W10 of the first portion 904 is greater than the width W20 of the second portion.

In some embodiments, a medical practitioner may modify or customize the device 900 prior to implantation into the body of the patient. For example, a medical practitioner may modify or customize the device 900 to best fit or to best serve the specific anatomy of the patient. In one embodiment, the first portion 904 of the device 900 may be cut, for example, along line Z1. In some embodiments, line Z1 extends at an angle with respect to the axis defined by the lumen 902. In some embodiments, line Z1 extends parallel or substantially parallel to an axis defined by the lumen 902. The medical practitioner may cut the device along line Z to effectively shorten the length of the first portion 904 that defines the lumen 902 (or in other words, to shorten the lumen 902). In some embodiments, a corresponding cut along line Z2 may also be made.

Figure 6A:
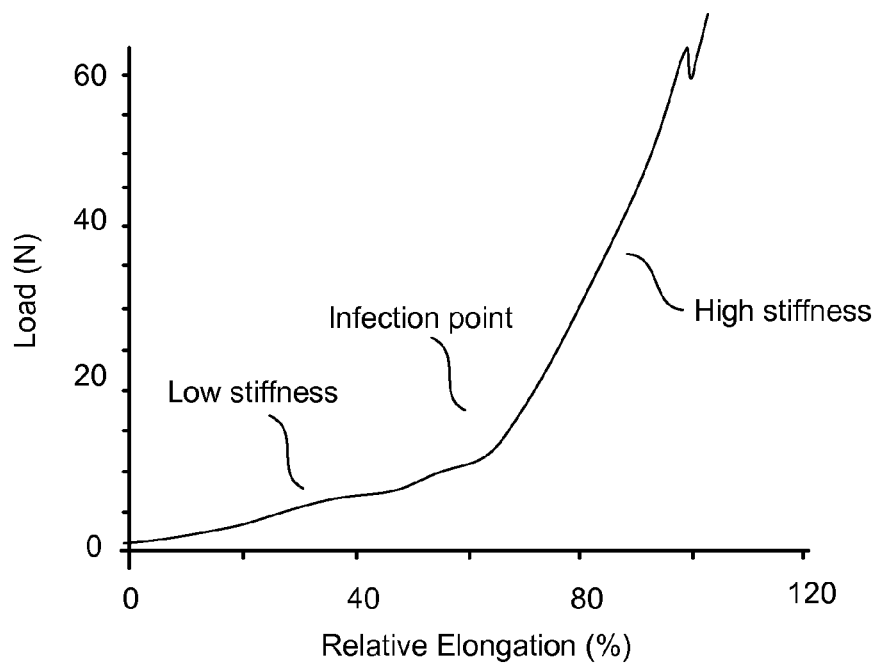
FIG. 6A is a graphical representation of relationship between stress applied on a vaginal tissue and resulting elongation in a vaginal tissue due to the applied stress.

FIG. 6A is an exemplary graphical representation of relationship between stress applied on a vaginal tissue and resulting elongation in the vaginal tissue due to the applied stress. A medical implant can be fabricated to conform to the changes resulting in the vaginal tissue due to applied stress. The medical implant can be any of the medical implants 200, 300, 400, and 500. The vaginal tissue is generally viscoelastic or viscohyperelastic. The vaginal tissue can experience large deformation under small loads as shown. Therefore, in some embodiments, the medical implant is configured to experience varying levels of deformation under varying loads. The vaginal tissue stress-strain or load vs (or compared to) elongation relationship can follow a non-linear curve as illustrated. The curve has a first linear phase at low loads/stresses. At low levels of load, the strains or elongations are high defining a low stiffness attribute of the implant. The curve includes a second phase defined by a transition phase after an inflection point where it transitions from one linear phase to a third phase such that the curve is sharper in the third phase. The third phase defines a region of relatively lower elongation even under an application of relatively higher loads as compared to the first phase. That is to say that that after the load increases after a limit defined by the inflection point, there is lesser elongation with every unit change in load. This defines a property of high stiffness of the implant at higher loads. The unit change in elongation with every unit change in load decreases thereafter till it reaches a level that there is almost negligible elongation in the implant even at increased loads. The implant thus behaves as a stiff member. Therefore, the medical implant can be configured to define the attributes congruent with the stress-strain or load vs (or compared to) elongation relationship of the vaginal tissue. In some embodiments, the portion of the medical implant attaching to the anterior or posterior portion of the vagina can be so configured that it experiences large deformations over small loads until the inflection point is achieved. As the load is increased beyond the inflection point, the medical implant portion attached to the anterior vaginal wall or posterior vaginal wall starts exhibiting high stiffness and very less (negligible) deformation.

Figure 6B:
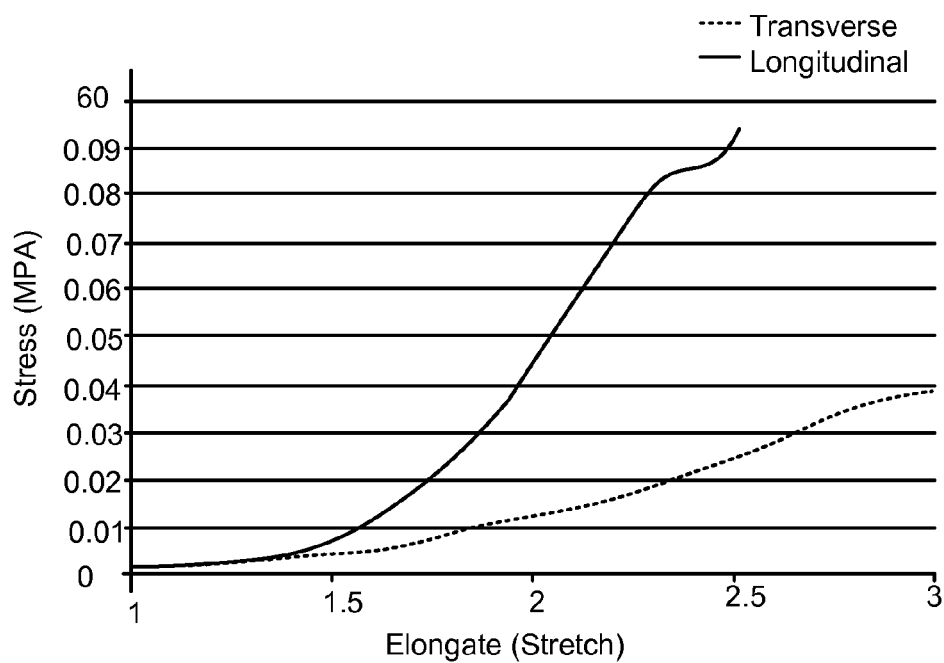
FIG. 6B is a graphical representation of a comparison of an exemplary attribute, elongation, of the vaginal tissue in a transverse direction and a longitudinal direction.

As mentioned with respect to FIGS. 2 and 3 above, in some cases the vaginal wall may be anisotropic in nature; therefore, it experiences different elongations in different directions. For example, the vaginal wall in a traverse direction is generally more elastic than in a longitudinal direction. Therefore, it may be desirable to configure the medical implant to exhibit values of the biomechanical attributes defined to emulate the varying elongation behavior of the vaginal wall in different directions. FIG. 6B is a graphical representation of a comparison of an exemplary attribute, elongation, of the vaginal tissue in the transverse direction (or non-transverse direction) and the longitudinal direction. A shown, the elongation of the vaginal tissue in the transverse direction (or non-transverse direction) is much lesser than the elongation in the longitudinal direction.

Referring to the graphical representations of FIGS. 6A-6B that depict the characteristics and behavior of a vaginal tissue, the portions of the medical implant that are attached to vaginal tissues are configured to behave accordingly in order to emulate the behavior of the vaginal tissues such as the anterior and posterior vaginal walls. For example, in some embodiments, the portions of the implant that attach to the anterior vaginal wall can be configured to define different stiffness characteristics at different levels of loads on the implant portions. Similarly, the implant portions that attach to the posterior vaginal wall can be configured to define different characteristics in different directions such as the transverse direction and the longitudinal direction and for different load values.

In some embodiments, stiffness at the low strain or deformation phase can range from 0.431-4.15 MPa for the anterior vaginal wall in the longitudinal direction. In some embodiments, stiffness at the high strain or deformation phase can range from 5.15-17.28 MPa for the anterior vaginal wall in the longitudinal direction. In some embodiments, stiffness at a low strain or deformation phase can range from 0.46-0.98 MPa for the posterior vaginal wall in the longitudinal direction. In some embodiments, stiffness at a high strain or deformation phase can range from 2.49-9.08 MPa for the posterior vaginal wall in the longitudinal direction. In some embodiments, stiffness at the low strain or deformation phase can range from 0.385-0.415 MPa for the anterior vaginal wall in the traverse direction. In some embodiments, stiffness at the high strain or deformation phase can range from 0.370-0.61 MPa for the anterior vaginal wall in the traverse direction. In some embodiments, stiffness at the low strain or deformation phase can range from 1.14-1.46 MPa for the posterior vaginal wall in the traverse direction. In some embodiments, stiffness at the high strain or deformation phase can range from 2.39-3.83 MPa for the posterior vaginal wall in the traverse direction. The values of stiffness detailed here are a guide for vaginal tissues generally. The values of stiffness can be different depending on disease state, age, or any other influencing factor. Therefore, the implant can be made/designed accordingly to be configured for emulating the biomechanical behavior of the vaginal tissue in accordance with the desired characteristic behavior.

Figure 7:
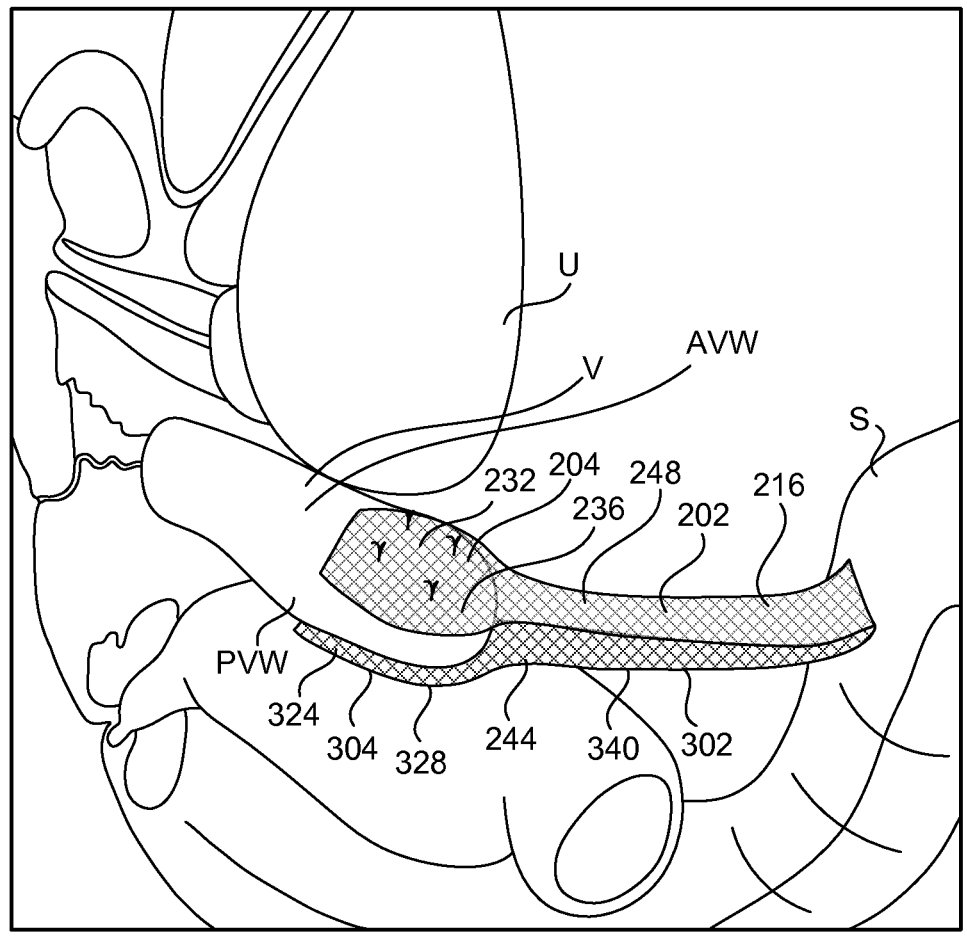
FIG. 7 is a perspective view of the medical implant of FIG. 2 and FIG. 3 placed inside a patient's body.
Figure 8:
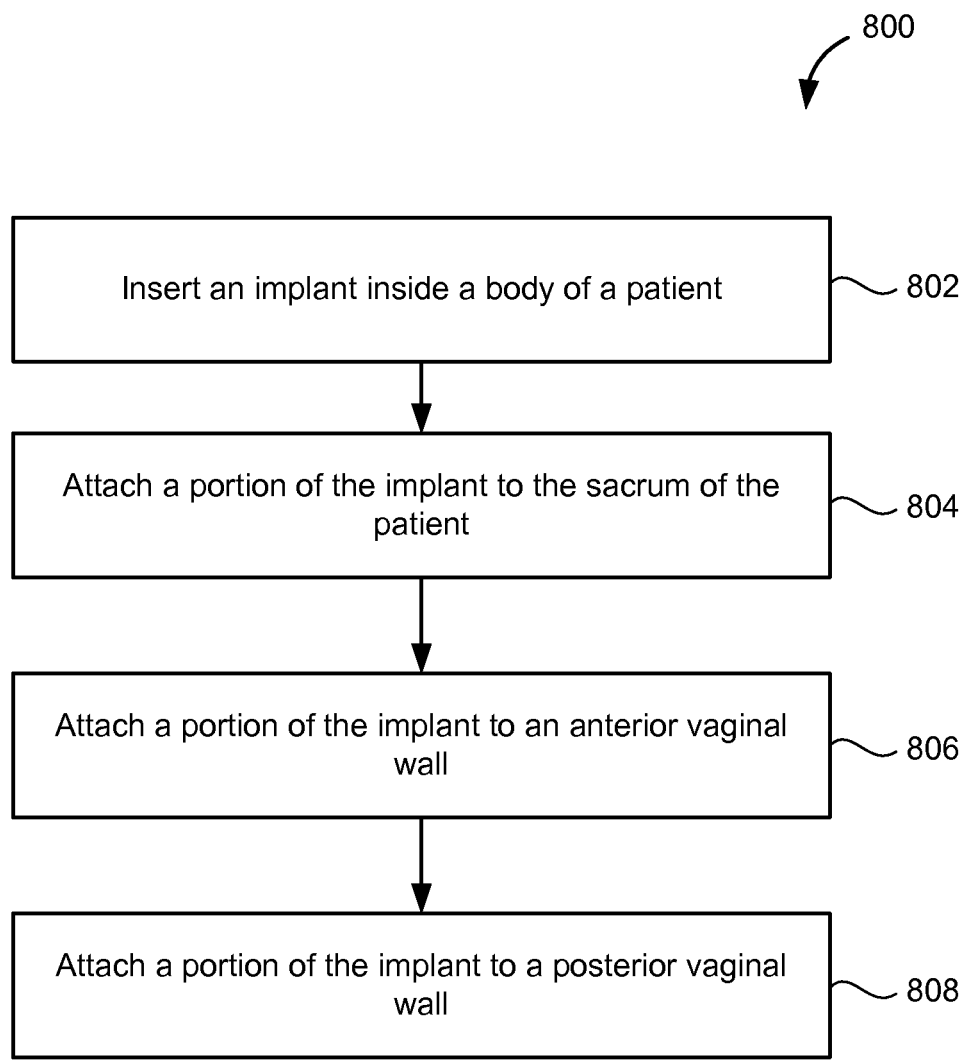
FIG. 8 is a flowchart illustrating a method for treatment of a pelvic floor disorder, in accordance with an embodiment of the present invention.

FIG. 7 is a perspective view of the medical implant 200, including the first flap 248 and the second flap 340 of FIG. 2 and FIG. 3 respectively, placed inside a patient's body, in accordance with an embodiment of the invention. The body portions of the patient such as the vagina V, the anterior vaginal wall AVW, the posterior vaginal wall PVW, a urethra U, and the sacrum S are illustrated in FIG. 7. FIG. 8 illustrates a method 800 for placing an implant in a patient's body. The method 800 is described below in conjunction with FIGS. 2, 3, 4, 5, and 7-9. The medical implant 200 including the first flap 248 and the second flap 340 is used as an exemplary embodiment to illustrate and discuss the method 800. However, it must be appreciated that other implants such as the medical implant 400, the medical implant 500, and the medical implant 900 as discussed above can also be employed equally.

The method 800 includes inserting the first flap 248 of the medical implant 200 inside the body at step 802. In some embodiments, the first flap 248 can be inserted inside the patient's body through a laparoscopic approach. In some embodiments, the method 800 includes creating an abdominal incision for delivering the medical implant inside the body laparoscopically.

The method 800 further includes attaching the first portion 202 of the medical implant 200 at the sacrum S inside the patient's body at step 803. The first portion 202 can be configured to define the biomechanical attributes so as to emulate the biomechanical behavior of the sacrum S in a defined set of physical conditions. The biomechanical attributes can be defined by the first set of values of respective biomechanical parameters associated with the biomechanical attributes.

The method 800 further includes attaching the second portion 204 of the first flap 248 to the anterior vaginal wall AVW at step 804. The anterior vaginal wall AVW is known to exhibit properties of viscoelasticity, anisotropy, and viscohyperelasticity. The second portion 204 can be configured to emulate the biomechanical behavior of the anterior vaginal wall AVW and define viscoelasticity, anisotropy, and viscohyperelasticity. The second portion 204 can define the biomechanical attributes that can be defined by the second set of values of respective biomechanical parameters associated with the biomechanical attributes as explained by way of FIG. 2. The first flap 248 is configured so that the first set of values is different from the second set of values. The difference in values can be attributed to the difference in the biomechanical behavior of the sacrum S and the anterior vaginal wall AVW. In some embodiments, the portion attaching to the anterior wall is formed monolithically with the first portion 202 and the transition region 206 as discussed above. It must be appreciated that any conventionally known or practiced methods or devices may be used for attaching the medical implant at any location inside the patient's body.

The method 800 further includes placing the second flap 340 of the medical implant 200 over the posterior vaginal wall PVW at step 806 as described below.

The first portion 302 can be configured to define the biomechanical attributes so as to emulate the biomechanical behavior of the sacrum S in a defined set of physical conditions. The biomechanical attributes can be defined by the first set of values of respective biomechanical parameters associated with the biomechanical attributes. The first set of values for the first portion 202 from the first flap 248 can be same as those for the first portion 302 from the second flap 340.

The posterior vaginal wall PVW is known to exhibit properties of viscoelasticity, anisotropy, and viscohyperelasticity. The second portion 304 can be configured to emulate the biomechanical behavior of the posterior vaginal wall PVW and define viscoelasticity, anisotropy, and viscohyperelasticity. The second portion 304 can define the biomechanical attributes that can be defined by the third set of values of respective biomechanical parameters associated with the biomechanical attributes as explained by way of FIG. 3. The second portion 304 can be configured to define the biomechanical attributes congruent to the biomechanical behavior of the posterior vaginal wall. The medical implant 200 can be fabricated so that second flap 340 is configured to have the third set of values corresponding to the biomechanical attributes to be different from the second set of values corresponding to the first flap 248. Therefore, the second portion 204 of the first flap 248 used for attaching to the anterior vaginal wall AVW defines a different set of values corresponding to a biomechanical parameter than the set of values corresponding to the same biomechanical parameter for the second portion 302 of the second flap 340 attaching to the posterior vaginal wall. In this way, the properties of the first flap 248 and the second flap 340 are different and congruent with respect to the portions the first flap 248 and the second flap 340 are attached to. In some embodiments, the portion attaching to the posterior vaginal wall PVW is formed monolithically with the first portion 302 and the transition region 306 as discussed above. It must be appreciated that any conventionally known or practiced methods or devices may be used for attaching the medical implant at any location inside the patient's body. In some embodiments, the tow flaps can be independent from each other and may collectively enable the medical implant 200 in emulating biomechanical behavior of the anterior vaginal wall AVW, posterior vaginal wall PVW and the sacrum S inside a patient's body.

In some embodiments, the method 800 further includes cutting an unwanted portion of the medical implant 200 after placing in the body. In some embodiments, the method 800 further includes closing the abdominal incision or any other incision created for method 800.

In some embodiments, the method 800 can be used for treatment of a pelvic floor disorder, in accordance with an embodiment of the present invention. The implant can be a dual knit mesh. The dual knit mesh material can be a polymer mesh, a polypropylene material, a bio-absorbable material, or any other preferred material. The knit structure defined by each of the implants 200, 400, and 500 can be any knit structure that emulates the biomechanical properties of the vagina in the wide body region and provides stiffness in the stem region. The implant can be sold as a separate dual knit mesh and a standard mesh. The implant can be used for vaginal prolapse to suspend the vagina to the sacral promontory or the sacrum after a hysterectomy termed as Sacrocolpopexy or any other disorders. The implant can be placed into the body by laparoscopic or any other means.

In some embodiments, an implant includes a first flap and a second flap. The first flap has a first portion configured to be attached proximate a sacrum; a second portion configured to be attached to an anterior vaginal wall; and a transition region lying between the first portion and the second portion. The second flap includes a portion configured to be attached to a posterior vaginal wall. A value corresponding to a biomechanical parameter defining a biomechanical attribute of the portion of the first flap attaching to the anterior wall is different from a value of the biomechanical parameter defining the biomechanical attribute of the portion of the second flap attaching to the posterior wall.

In some embodiments, the portions of the implant may be coupled to the portions of the body in any order. For example, in some embodiments, the implant is coupled to the vaginal wall and then the implant is coupled to the sacrum or to tissue proximate the sacrum. In other embodiments, the implant is coupled to the sacrum or tissue proximate the sacrum and then the implant is coupled to the vaginal wall.

In some embodiments, an implant includes a first end portion, a second end portion and a body in between the ends. The first end portion has a biomechanical attribute that is different in value than the same biomechanical attribute at the second end portion.

In some embodiments, the first portion of the first flap defines a first type of knit structure. In some embodiments, the second portion of the first flap defines a second type of knit structure. In some embodiments, the first type of knit structure includes pores that are smaller in cross sectional profile than the pores in the second type of knit structure. In some embodiments, a width of the second portion is substantially more or greater than a width of the first portion of the first flap. In some embodiments, the second portion includes a proximal end and a distal end, the distal end being proximate the transition region, wherein the width of the second portion varies from the proximal end to the distal end of the second portion. In some embodiments, the varying second width along the second portion defines a trapezoidal shape of the second portion. In some embodiments, the transition region defines a third type of knit structure. In some embodiments, each of the first and the second flaps defines a planar shape and are configured to be attached separately to bodily locations. In some embodiments, each of the value of the biomechanical parameter defining the biomechanical attribute of the portion of the first flap attaching to the anterior wall and the value of the biomechanical parameter defining the biomechanical attribute of the portion of the second flap attaching to the posterior wall is different from a value of the biomechanical parameter of the first portion attaching proximate the sacrum.

In some embodiments, the biomechanical attribute is elasticity and the biomechanical parameter is a modulus of elasticity. In some embodiments, the biomechanical attribute is viscoelasticity. In some embodiments, the biomechanical attribute is viscohyperelasticity. In some embodiments, the biomechanical attribute is anisotropicity. In some embodiments, the biomechanical attribute is resistance to creep. In some embodiments, the biomechanical attribute is stiffness.

In some embodiments, the second flap includes a first portion defining a width and configured to be attached proximate the sacrum; a second portion defining a width and configured to be attached to the posterior vaginal wall; and a transition region lying between the first portion and the second portion and monolithically joining the first portion and the second portion.

In some embodiments, the first flap and the second flap are constructed from a single piece of material. In some embodiments, the first flap and the second flap are fabricated independent of each other. In some embodiments, each of the first flap and the second flap are fabricated from a linear strip of material such that the transition region of each of the first flap and the second flap extends monolithically from each of the first portion, and the second portion.

In some embodiments, a tubular implant includes a first portion of the tubular implant configured to be attached proximate a sacrum; a transition region extending from the first portion; a second portion of the tubular implant and extending from the transition region monolithically and including a first section and a second section and two slits provided laterally in the second portion configuring the first section as apart from the second section at a proximal end; and a lumen defined within the first and second portions of the tubular implant. The first section is configured to be attached to an anterior vaginal wall, and the second section is configured to be attached to a posterior vaginal wall.

In some embodiments, a knit structure of the first portion is different from a knit structure of the second portion. In some embodiments, a knit structure of the first section is different from a knit structure of the second section of the section portion. In some embodiments, a value corresponding to a biomechanical parameter defining a biomechanical attribute of the first section wall is different from a value of the biomechanical parameter of the second section.

In some embodiments, a method for placing an implant in a body of a patient, the method includes inserting the implant inside the body; attaching a portion of the implant to an anterior vaginal wall, wherein the portion attaching to the anterior vaginal wall defines a first value of a biomechanical parameter defining a biomechanical attribute; attaching a portion of the implant to a posterior vaginal wall, wherein the portion attaching to the posterior vaginal wall defines a second value of the biomechanical parameter such that the second value corresponding to the portion attaching to the posterior wall is different from the first value corresponding to the portion attaching to the anterior wall.

In some embodiments, the method includes creating an abdominal incision for delivering the implant inside the body laparoscopically. In some embodiments, the portions attaching to the anterior wall, and the posterior wall define regions of a tubular structure of the implant. In some embodiments, the tubular structure includes a portion configured to be attached proximate a sacrum, the method further comprising attaching the portion proximate the sacrum.

In some embodiments, the portion attaching to the anterior wall is formed monolithically with a second portion configured to be attached proximate a sacrum and a transition region between the portion attaching to the anterior wall and the second portion attaching proximate the sacrum, the method further comprising attaching the second portion proximate the sacrum. In some embodiments, the portion attaching to the posterior wall is formed monolithically with a second portion configured to be attached proximate a sacrum and a transition region between the portion attaching to the posterior wall and the second portion attaching proximate the sacrum, the method further comprising attaching the second portion proximate the sacrum.

In some embodiments, the method includes cutting an unwanted portion of the implant after placing in the body. In some embodiments, the method includes closing the abdominal incision and other incisions.

In some embodiments, an implant includes a first portion having a tubular structure and defining a lumen; and a second portion extending from the first portion, the first portion having a stiffness that is greater than a stiffness of the second portion.

In some embodiments, the second portion includes a first flap coupled to the first portion and a second flap coupled to the first portion. In some embodiments, the second portion includes a first flap coupled to the first portion and a second flap coupled to the first portion, the first flap having a stiffness that is different than the stiffness of the first portion. In some embodiments, the stiffness of the first flap is greater than the stiffness of the first portion. In some embodiments, the first portion is formed from a mesh material. In some embodiments, the second portion is formed of a mesh material. In some embodiments, the first portion is configured to be attached to a sacrum of a patient.

In some embodiments, the second portion includes a first flap and a second flap, the first portion is configured to be attached near a sacrum of a patient, the first flap is configured to be attached to an anterior vaginal wall of the patient, the second flap is configured to be attached to a posterior vaginal wall of the patient. In some embodiments, the first portion is formed of a mesh material, the mesh material having side edges, the side edges of the mesh material being disposed within the lumen defined by the first portion.

In some embodiments, an implant includes a first portion having a tubular structure and defining a lumen; and a second portion having a first flap and a second flap, the first flap being coupled to the first portion, the second flap being coupled to the first portion.

In some embodiments, the first flap is coupled to an end portion of the first portion via a suture. In some embodiments, the first portion has a stiffness, the first flap has a stiffness, the stiffness of the first portion is different than the stiffness of the first flap. In some embodiments, the stiffness of the first portion is greater than the stiffness of the first flap. In some embodiments, the first portion has a width, the second portion has a width, the width of the second portion being greater than the width of the first portion. In some embodiments, the first portion is formed of a mesh material. In some embodiments, the first flap is formed of a mesh material.

In some embodiments, a method of placing an implant within a body of a patient includes providing an implant including a first portion having a tubular structure and defining a lumen and a second portion extending from the first portion, the lumen defining an axis; cutting a portion of the first portion of the implant along a line that is substantially parallel to the axis defined by the lumen; and placing the implant within the body of the patient.

In some embodiments, the placing the implant within the body of the patient through an abdominal incision. In some embodiments, the placing the implant within the body of the patient includes attaching a portion of the first portion of the implant to a sacrum of the patient. In some embodiments, the placing the implant within the body of the patient includes attaching the second portion of the implant to a vaginal wall of the patient. In some embodiments, the second portion includes a first flap and a second flap, the placing the implant within the body of the patient includes attaching the first flap to an anterior vaginal wall of the patient and attaching the second flap to a posterior vaginal wall of the patient. In some embodiments, the first portion of the implant has a stiffness that is greater than the second portion of the implant.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:
1. An implant, comprising:
   a first mesh portion having a first tubular portion, the first mesh portion having a first end portion defining a first opening and a second end portion defining a second opening, the first mesh portion defining a lumen between the first opening and the second opening, the first mesh portion configured to be attached to a sacrum of a patient;
   and a second mesh portion having a second tubular portion, the second tubular portion having a first lateral slit and a second lateral slit, the second tubular portion having a first flap coupled to the first end portion of the first mesh portion and a second flap coupled to the first end portion of the first mesh portion, the first flap configured to be attached to an anterior vaginal wall of the patient, the second flap configured to be attached to a posterior vaginal wall of the patient,
   the first mesh portion having a stiffness that is greater than a stiffness of the second mesh portion.
2. The implant of claim 1, wherein the first flap has a stiffness that is different than the stiffness of the first mesh portion.
3. The implant of claim 2, wherein the stiffness of the first flap is less than the stiffness of the first mesh portion.
4. The implant of claim 1, wherein the first mesh portion and the second mesh portion are separate mesh constructs but coupled together with stitching.

5. The implant of claim 1, wherein the first mesh portion has side edges, the side edges being disposed within the lumen defined by the tubular structure.

6. An implant, comprising:
- a first tubular portion having a first end portion and a second end portion, the first end portion defining a first opening, the second end portion defining a second opening, the first tubular portion defining a lumen extending between the first opening and the second opening; and
- a second tubular portion having a first lateral slit and a second lateral sit, the second tubular portion including:
  - a first flap coupled to the first end portion of the first tubular portion, the first flap being coupled to the first end portion via a suture; and
  - a second flap coupled to the first end portion of the first tubular portion.

7. The implant of claim 6, wherein the first tubular portion has a stiffness, and the first flap has a stiffness, the stiffness of the first tubular portion being different than the stiffness of the first flap.

8. The implant of claim 7, wherein the stiffness of the first tubular portion is greater than the stiffness of the first flap.

9. The implant of claim 6, wherein the first tubular portion is formed of a mesh material.

10. The implant of claim 6, wherein the first flap is formed of a mesh material.

11. A method of placing an implant within a body of a patient, comprising:
- providing a mesh implant including a tubular structure having a first tubular portion, and a second tubular portion, the second tubular portion having a first lateral slit and a second lateral slit, the second tubular portion having a first flap, and a second flap, the first tubular portion having a first end portion and a second end portion, the first tubular portion defining a lumen between and through the first end portion and the second end portion, the lumen defining an axis, the first flap being coupled to the first end portion, the second flap being coupled to the first end portion; and
- placing the implant within the body of the patient including attaching a portion of the first tubular portion to a sacrum of the patient.

12. The method of claim 11, further comprising creating an abdominal incision, and placing the implant within the body of the patient through the abdominal incision.

13. The method of claim 11, wherein the placing the implant within the body of the patient further includes attaching a portion of the first flap to an anterior vaginal wall of the patient, and attaching a portion of the second flap to a posterior vaginal wall of the patient.

14. The method of claim 11, further comprising:
- cutting the first end portion of the first tubular portion at a location between the first flap and the second flap in a direction towards the second end portion of the first tubular portion, wherein the cutting increases an effective length of the first and second flaps.

* * * * *